United States Patent
MacLeod et al.

(10) Patent No.: US 6,174,879 B1
(45) Date of Patent: Jan. 16, 2001

(54) AMINOCYCLOHEXYLESTERS AND USES THEREOF

(75) Inventors: Bernard A. MacLeod; Michael J. A. Walker; Richard A. Wall, all of Vancouver (CA)

(73) Assignee: University of British Columbia (CA)

( * ) Notice: Under 35 U.S.C. 154(b), the term of this patent shall be extended for 0 days.

(21) Appl. No.: 09/271,087

(22) Filed: Mar. 17, 1999

Related U.S. Application Data

(62) Division of application No. 08/807,728, filed on Feb. 27, 1997, now Pat. No. 5,885,984, which is a division of application No. 08/313,691, filed on Sep. 27, 1994, now Pat. No. 5,637,583, which is a continuation-in-part of application No. 08/126,575, filed on Sep. 24, 1993, now abandoned.

(51) Int. Cl.$^7$ ........................ C07D 211/22; C07D 211/24; C07D 223/04; A61K 31/44; A61K 31/55
(52) U.S. Cl. .............................. 514/212.01; 514/217.12; 514/319; 514/320; 514/327; 514/317; 514/408; 514/422; 514/429; 540/450; 540/451; 540/480; 540/524; 540/526; 540/596; 540/602; 540/604; 540/484; 540/200; 540/354; 540/362; 546/192; 546/195; 546/196; 546/216; 548/950; 548/952; 548/517; 548/527; 548/541; 548/572
(58) Field of Search ...................................... 540/450, 451, 540/480, 524, 526, 596, 602, 604, 484, 200, 354, 362; 548/950, 952, 517, 527, 541, 572; 546/192, 195, 146, 216; 514/210, 212, 319, 320, 327, 317, 408, 422, 429

(56) References Cited

U.S. PATENT DOCUMENTS

| | | | |
|---|---|---|---|
| 2,954,380 | 9/1960 | Shapiro et al. | 260/268 |
| 4,438,130 | 3/1984 | Kaplan | 424/274 |
| 4,656,182 | 4/1987 | Horwell | 514/324 |
| 4,737,493 | 4/1988 | Horwell | 514/212 |
| 4,855,316 | 8/1989 | Horwell et al. | 514/422 |

FOREIGN PATENT DOCUMENTS

| | | |
|---|---|---|
| 121 972 A2 | 10/1965 | (EP) . |
| 1389414 | 2/1965 | (FR) . |
| 2689893 | 10/1993 | (FR) . |
| 52-019637 | 2/1977 | (JP) . |
| WO 86/07257 | 12/1986 | (WO) . |

OTHER PUBLICATIONS

Halfpenny et al. (J. Med. Chem. (1989), 32(7), 1620–1626).*

Munk et al. (J. Org. Chem. (1968), 33(9), 3480–6).*

Abraham et al., "Antiarrhythmic Properties of Tetrodotoxin Against Occlusion–Induced Arrhythmias in the Rat: A Novel Approach to the Study of the Antiarrhythmic Effects of Ventricular Sodium Channel Blockade," *J. Pharmacol. Exp. Ther.* 251(3):1166–1173, 1989.

Curtis and Walker, "Quantification of arrhythmias using scoring systems: an examination of seven scores in an in vivo model of regional myocardial ischaemia," *Cardiovasc. Res.* 22:656–665, 1988.

Hall, Jr. et al., "Aminomercuration of Olefins," *Journal of Organic Chemistry* 37(20):3069–3075, 1972.

Laboratori Farmaceutici A. Malizia S.p.A., "Esters of 4–piperidinocyclohexanol," *Chemical Abstracts 63*: 1773b, 1965.

Laboratori Farmaceutici A. Malizia S.p.A., "Piperidine–n–cyclohexanol esters," Derwent Abstract No. 66–16021F, 1966.

Penz et al., "A New ECG Measure (RSh) for Detecting Possible Sodium Channel Blockade in Vivo in Rats," *J. Pharmacol. Methods* 27(1):51–58, 1992.

Pugsley et al., "Antiarrhythmic effects of U–50,488H in rats subject to coronary artery occlusion," *Eur. J. Pharmacol.* 212:15–19, 1992.

Pugsley et al., "Cardiovascular actions of the kappa.–agonist, U–50,488H, in the absence and presence of opioid receptor blockade," *Br. J. Pharmacol.* 105:521–526, 1992.

Pugsley et al., "Cardiovascular Actions of U50,488H and Related Kappa Agonists," *Cardiovascular Drug Reviews* 11(2):151–164, 1993.

Pugsley et al., "Electrophysiological and antiarrhythmic actions of the .kappa. agonist PD 129290, and its R,R (+)–enantiomer, PD 129289," *Br. J. Pharmacol.* 110:1579–1585, 1993.

Shapiro et al., "Aminocyclohexyl Esters," *Journal of the American Chemical Society* 81:3993–3996, 1959.

\* cited by examiner

*Primary Examiner*—Bruck Kifle
(74) *Attorney, Agent, or Firm*—SEED Intellectual Property Law Group PLLC

(57) ABSTRACT

Aminocyclohexylester compounds, including thioesters, are disclosed. The compounds of the present invention may be incorporated in compositions and kits. The present invention also discloses a variety of in vitro and in vivo uses for the compounds and compositions, including the blockade of ion channels and the treatment of arrhythmias.

16 Claims, No Drawings

AMINOCYCLOHEXYLESTERS AND USES THEREOF

This application is a divisional of U.S. patent application Ser. No. 08/807,728, filed Feb. 27, 1997, which issued as U.S. Pat. No. 5,885,984; which application is a divisional of U.S. application Ser. No. 08/313,691, filed Sep. 27, 1994, which issued as U.S. Pat. No. 5,637,583; which application is a continuation-in-part of U.S. application Ser. No. 08/126,575, filed Sep. 24, 1993, abandoned.

TECHNICAL FIELD

The present invention is generally directed toward aminocyclohexylester compounds, including thioesters, for use in cardiac arrhythmias, the blockade of ion channels and the preparation of pharmaceutical compositions and kits.

BACKGROUND OF THE INVENTION

Arrhythmia is a variation from the normal rhythm of the heart beat. The major cause of fatalities due to cardiac arrhythmias is the subtype of arrhythmias known as ventricular fibrillation. Conservative estimates indicate that, in the U.S. alone, approximately 300,000 individuals per year suffer heart attacks. Approximately half of these die from sudden cardiac death, the major cause of which is ventricular fibrillation.

Antiarrhythmic agents have been developed to prevent or alleviate cardiac arrhythmia. For example, Class I antiarrhythmic compounds have been used to treat supraventricular arrhythmias and ventricular arrhythmias. Treatment of ventricular arrhythmia is very important since such an arrhythmia, especially ventricular fibrillation, can be fatal. Serious ventricular arrhythmias (ventricular tachycardia and ventricular fibrillation) occur most often in the presence of myocardial ischemia and/or infarction. Ventricular fibrillation often occurs in the setting of acute myocardial ischemia, before infarction fully develops. At present, lidocaine is the current drug of choice for prevention of ventricular fibrillation. However, many Class I antiarrhythmic compounds may actually increase mortality in patients who have had a myocardial infarction. Therefore, there is a need in the art to identify new antiarrhythmic treatments, particularly treatments for ventricular arrhythmias. The present invention fulfills this need, and further provides other related advantages.

SUMMARY OF THE INVENTION

Briefly stated, the present invention provides compounds for a variety of uses. including the blockade of ion channels in vitro and in vivo, and for the treatment of arrhythmias In an aspect of the present invention, aminocyclohexyl esters and thioesters are provided. In one embodiment, a compound comprises an enantiomer or geometric isomer of a compound of formula I, or a solvate or pharmaceutically acceptable salt thereof, the compound of the formula:

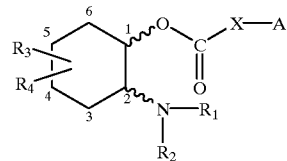

(I)

wherein X is a direct bond;

or —$(CH_2)_n$—Y—, where n=1, 2, or 3, and Y is a direct bond, O or S;

or —$CH(R_{12})$—Y—, where $R_{12}$ is alkyl of from one to six carbon atoms, a saturated carbocyclic ring of from three to six carbon atoms, phenyl or benzyl, and Y is a direct bond, O or S;

or —$C(R_{13})$=CH—, where $R_{13}$ is hydrogen, alkyl of from one to six carbon atoms, or phenyl;

$R_1$ and $R_2$ are independently hydrogen, alkyl of three to eight carbon atoms, alkoxyalkyl of three to eight carbon atoms, or aralkyl of seven to twelve carbon atoms;

or $R_1$ and $R_2$, when taken together with the nitrogen atom to which they are attached, form a ring denoted by formula II:

(II)

where m is an integer from three to eight, and the ring may be substituted at any one carbon atom by hydroxy, oxo, alkyl of one to three carbon atoms or alkoxy of one to three carbon atoms, or may be fused at two adjacent carbon atoms with an aromatic or aliphatic carbocyclic ring of six carbon atoms;

or complete a saturated monocyclic nitrogen heterocyclic ring of five to eight ring atoms, containing only carbon, nitrogen and optionally oxygen ring atoms, and the heterocyclic ring containing not more than two nitrogen ring atoms, the second nitrogen being optionally substituted with an alkyl group of one to six carbon atoms or a phenyl ring;

or complete a ring selected from 3-azabicyclo[3.2.2] nonan-3-yl, 2-azabicyclo[2.2.2]octan-2-yl, 3-azabicyclo[3.1.0]hexan-3-yl, or 3-azabicyclo[3.2.0] heptan-3-yl;

$R_3$ and $R_4$ are independently attached to the cyclohexane ring at the 3-, 4-, 5-, or 6-positions, and are independently hydrogen, hydroxy, alkyl of one to six carbon atoms or alkoxy of one to six carbon atoms, or are points of attachment of a spiro five- or six-membered heterocyclic ring containing one oxygen or sulfur atom; and A is an alkyl group of five to twelve carbon atoms, or is a saturated carbocyclic ring of three to six carbon atoms, or is selected from formulae III, IV, V, VI, VII or VII:

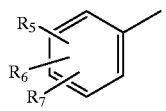

(III)

where $R_5$, $R_6$ and $R_7$ are independently hydrogen, hydroxy, amino, fluorine, chlorine, bromine, nitro, trifluoromethyl, alkyl of one to six carbon atoms, alkoxy of one to six carbon atoms, or aryl, and when X is a direct bond at least one of $R_5$, $R_6$ and $R_7$ is a hydroxy, fluorine, chlorine, bromine, trifluoromethyl, alkyl of from one to six carbon atoms, or aryl substituent, and when X is —CH=CH—, and $R_1$ and $R_2$ when taken together with the nitrogen atom to which they are attached, form a N-phenylpiperazine ring, and $R_3$ and $R_4$ are hydrogen, at least one of $R_5$, $R_6$ and $R_7$ is a substituent other than hydrogen;

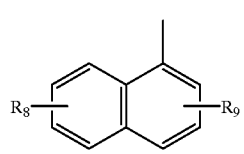

(IV)

where $R_8$ and $R_9$ are independently hydrogen, hydroxy, fluorine, chlorine, bromine, alkyl of one to six carbon atoms, alkoxy of one to six carbon atoms or aryl;

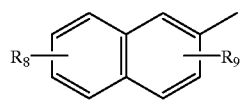

(V)

where $R_8$ and $R_9$ are defined as above;

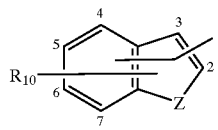

(VI)

where $R_{10}$ is hydrogen, hydroxy, fluorine, chlorine, bromine, alkyl of from one to six carbon atoms, alkoxy of from one to six carbon atoms, or aryl; Z is $CH_2$, O, S, or N—$R_{11}$ where $R_{11}$ is hydrogen or alkyl of one to six carbon atoms;

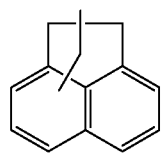

(VII)

only when X is a direct bond;

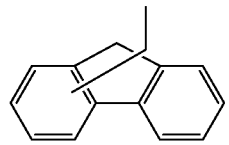

(VIII)

only when X is a direct bond;
with the proviso that, when X is —$(CH_2)_n$—Y—, and n=1, and Y is a direct bond, and $R_1$ and $R_2$, when taken together with the nitrogen atom to which they are attached, form a pyrrolidinyl ring, and $R_3$ and $R_4$ are hydrogen, A may not be 4-thianaphthenyl.

In another embodiment, a compound comprises an enantiomer or geometric isomer of a compound of formula I, or a solvate or pharmaceutically acceptable salt thereof, the compound of the formula:

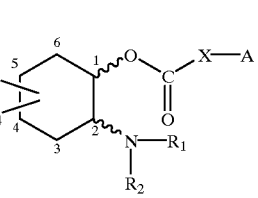

(I)

wherein X is a direct bond;
or —$(CH_2)_n$—Y—, where n=1 and Y is a direct bond, O or S;
or —$CH(R_{12})$—, where $R_{12}$ is alkyl of from one to six carbon atoms;
or —$C(R_{13})$=CH—, where $R_{13}$ is hydrogen;
$R_1$ and $R_2$ are independently hydrogen, alkyl of three to eight carbon atoms, alkoxyalkyl of three to eight carbon atoms, or aralkyl of seven to twelve carbon atoms;
or $R_1$ and $R_2$, when taken together with the nitrogen atom to which they are attached, form a ring denoted by formula II:

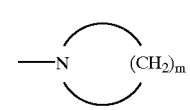

(II)

where m is an integer from three to eight, and the ring may be substituted at any one carbon atom by hydroxy, oxo, alkyl of one to three carbon atoms or alkoxy of one to three carbon atoms, or may be fused at two adjacent carbon atoms with an aromatic or aliphatic carbocyclic ring of six carbon atoms;
or complete a saturated monocyclic nitrogen heterocyclic ring of five to eight ring atoms, containing only carbon, nitrogen and optionally oxygen ring atoms, and the heterocyclic ring containing not more than two nitrogen ring atoms, the second nitrogen being optionally substituted with an alkyl group of one to six carbon atoms or a phenyl ring;
or complete a ring selected from 3-azabicyclo[3.2.2] nonan-3-yl, 2-azabicyclo[2.2.2]octan-2-yl, 3-azabicyclo[3.1.0]hexan-3-yl, or 3-azabicyclo[3.2.0] heptan-3-yl;

$R_3$ and $R_4$ are independently attached to the cyclohexane ring at the 3-, 4-, 5-, or 6-positions, and are independently hydrogen, hydroxy, alkyl of one to six carbon atoms or alkoxy of one to six carbon atoms, or are points of attachment of a spiro five- or six-membered heterocyclic ring containing one oxygen or sulfur atom; and A is an alkyl group of five to twelve carbon atoms, or is a saturated carbocyclic ring of three to six carbon atoms, or is selected from:

formula III where $R_5$, $R_6$ and $R_7$ are independently hydrogen, hydroxy, amino, fluorine, chlorine, bromine, nitro, trifluoromethyl, alkyl of one to six carbon atoms, alkoxy of one to six carbon atoms, or aryl, and when X is a direct bond at least one of $R_5$, $R_6$ and $R_7$ is a hydroxy, fluorine, chlorine, bromine, trifluoromethyl, alkyl of from one to six carbon atoms, or aryl substituent, and when X is —CH=CH—, and $R_1$ and $R_2$, when taken together with the nitrogen atom to which they are attached, form a N-phenylpiperazine ring, and $R_3$ and $R_4$ are hydrogen, at least one of $R_5$, $R_6$ and $R_7$ is a substituent other than hydrogen;

or formula IV where $R_8$ and $R_9$ are independently hydrogen, hydroxy, fluorine, chlorine, bromine, alkyl of one to six carbon atoms, alkoxy of one to six carbon atoms or aryl;

or formula V where $R_8$ and $R_9$ are defined as above;

or formula VI where $R_{10}$ is hydrogen, hydroxy, fluorine, chlorine, bromine, alkyl of from one to six carbon atoms, alkoxy of from one to six carbon atoms, or aryl; Z is $CH_2$, O, S, or N—$R_{11}$ where $R_{11}$ is hydrogen or alkyl of one to six carbon atoms;

or formula VII only when X is a direct bond;

or formula VIII only when X is a direct bond;

with the proviso that, when X is —$(CH_2)_n$—Y—, and n=1, and Y is a direct bond, and $R_1$ and $R_2$, when taken together with the nitrogen atom to which they are attached, form a pyrrolidinyl ring, and $R_3$ and $R_4$ are hydrogen, A may not be 4-thianaphthenyl.

In another embodiment, a compound comprises an enantiomer or geometric isomer of a compound of formula I, or a solvate or pharmaceutically acceptable salt thereof, the compound of the formula:

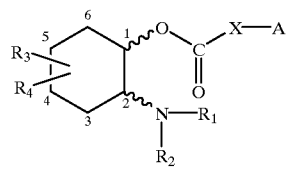

(I)

wherein X is —$(CH_2)_n$—Y—, where n=1 and Y is a direct bond or O;

or —$CH(R_{12})$—, where $R_{12}$ is alkyl of from one to six carbon atoms;

$R_1$ and $R_2$ are defined as in formula I as first described herein;

$R_3$ and $R_4$ are independently attached to the cyclohexane ring at the 4- or 5-positions, and are independently hydrogen, alkoxy of one to six carbon atoms, or are points of attachment of a spiro five- or six-membered heterocyclic ring containing one oxygen atom; and A is an alkyl group of five to twelve carbon atoms, or is a saturated carbocyclic ring of three to six carbon atoms, or is selected from:

formula III where $R_5$, $R_6$ and $R_7$ are independently hydrogen, hydroxy, amino, fluorine, chlorine, bromine, nitro, trifluoromethyl, alkyl of one to six carbon atoms, alkoxy of one to six carbon atoms, or aryl;

or formula IV where $R_8$ and $R_9$ are independently hydrogen, hydroxy fluorine, chlorine, bromine, alkyl of one to six carbon atoms, alkoxy of one to six carbon atoms or aryl;

or formula V where $R_8$ and $R_9$ are defined as above;

or formula VI where $R_{10}$ is hydrogen, hydroxy, fluorine, chlorine, bromine, alkyl of from one to six carbon atoms, alkoxy of from one to six carbon atoms, or aryl; Z is $CH_2$, O, S, or N—$R_{11}$ where $R_{11}$ is hydrogen or alkyl of one to six carbon atoms;

with the proviso that, when X is —$(CH_2)_n$—Y—, and n=1, and Y is a direct bond, and $R_1$ and $R_2$, when taken together with the nitrogen atom to which they are attached, form a pyrrolidinyl ring, and $R_3$ and $R_4$ are hydrogen, A may not be 4-thianaphthenyl.

In another embodiment, a compound comprises an enantiomer or geometric isomer of a compound of formula IX, or a solvate or pharmaceutically acceptable salt thereof, the compound of the formula:

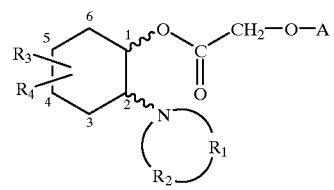

(IX)

wherein $R_1$ and $R_2$, when taken together with the nitrogen atom to which they are attached, either form a ring according to formula II, where m is an integer from three to eight, and the ring may be substituted at any one carbon atom by hydroxy, oxo, alkyl of one to three carbon atoms or alkoxy of one to three carbon atoms, or may be fused at two adjacent carbon atoms with an aromatic or aliphatic carbocyclic ring of six carbon atoms;

or complete a saturated monocyclic nitrogen heterocyclic ring of five to eight ring atoms, containing only carbon, nitrogen and optionally oxygen ring atoms, and the heterocyclic ring containing not more than two nitrogen ring forming atoms, the second nitrogen being optionally substituted with an alkyl group of one to six carbon atoms or a phenyl ring;

or complete a ring selected from 3-azabicyclo[3.2.2]nonan-3-yl, 2-azabicyclo[2.2.2]octan-2-yl, 3-azabicyclo[3.1.0]hexan-3-yl, or 3-azabicyclo[3.2.0]heptan-3-yl;

$R_3$ and $R_4$ are independently attached to the cyclohexane ring at the 4- or 5-positions, and are independently hydrogen, methoxy, or are points of attachment of a five-membered oxaspiran ring; and A is a saturated carbocyclic ring of three to six carbon atoms, or is selected from:

formula III where $R_5$ is hydrogen, and $R_6$ and $R_7$ are independently hydrogen, hydroxy, amino, fluorine, chlorine, bromine, nitro, trifluoromethyl, methyl, ethyl, methoxy, or ethoxy, and at least one of $R_6$ and $R_7$ is a substituent other than hydrogen;

or formula IV where $R_8$ and $R_9$ are hydrogen;

or formula V where $R_8$ and $R_9$ are hydrogen;

or formula VI where $R_{10}$ is hydrogen, and Z is $CH_2$, O, S, or N—$R_{11}$ where $R_{11}$ is hydrogen or methyl.

In another embodiment, a compound comprises an enantiomer or geometric isomer of a compound of formula X, or a solvate or pharmaceutically acceptable salt thereof, the compound of the formula:

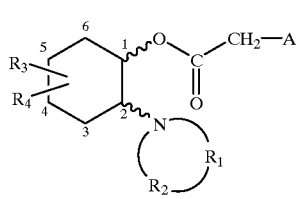

(X)

wherein $R_1$ and $R_2$, when taken together with the nitrogen atom to which they are attached, form a ring denoted as in formula II, where m is an integer from three to eight, and the ring may be substituted at any one carbon atom by hydroxy, oxo, alkyl of one to three carbon atoms or alkoxy of one to three carbon atoms, or may be fused at two adjacent carbon atoms with an aromatic or aliphatic carbocyclic ring of six carbon atoms;

or complete a saturated monocyclic nitrogen heterocyclic ring of five to eight ring atoms, containing only carbon, nitrogen and optionally oxygen ring atoms, and the heterocyclic ring containing not more than two nitrogen ring atoms, the second nitrogen being optionally substituted with an alkyl group of one to six carbon atoms or a phenyl ring;

or complete a ring selected from 3-azabicyclo[3.2.2]nonan-3-yl, 2-azabicyclo[2.2.2]octan-2-yl, 3-azabicyclo[3.1.0]hexan-3-yl, or 3-azabicyclo[3.2.0]heptan-3-yl;

$R_3$ and $R_4$ are independently attached to the cyclohexane ring at the 4- or 5-positions, and are independently hydrogen, methoxy, or are points of attachment of a five-membered oxaspiran ring; and A is a saturated carbocyclic ring of from three to six carbon atoms, or is selected from:

formula III where $R_5$ is hydrogen, and $R_6$ and $R_7$ are independently hydrogen, hydroxy, amino, fluorine, chlorine, bromine, nitro, trifluoromethyl, methyl, ethyl, methoxy, or ethoxy, and at least one of $R_6$ and $R_7$ is a substituent other than hydrogen;

or formula IV where $R_8$ and $R_9$ are hydrogen;

or formula V where $R_8$ and $R_9$ are hydrogen;

or formula VI where $R_{10}$ is hydrogen, and Z is $CH_2$, O, S, or N—$R_{11}$ where $R_{11}$ is hydrogen or methyl;

with the proviso that when $R_1$ and $R_2$, taken together with the nitrogen atom to which they are attached, form a pyrrolidinyl ring, and $R_3$ and $R_4$ are hydrogen, A may not be 4-thianaphthenyl.

In another embodiment, a compound comprises an enantiomer or geometric isomer of a compound of formula I, or a solvate or pharmaceutically acceptable salt thereof, the compound of the formula:

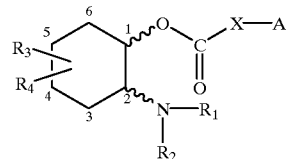

(I)

wherein X is a direct bond or —CH=CH—;

$R_1$ and $R_2$ are independently hydrogen, alkyl of three to eight carbon atoms, alkoxyalkyl of three to eight carbon atoms, or aralkyl of seven to twelve carbon atoms;

or $R_1$ and $R_2$, when taken together with the nitrogen atom to which they are attached, form a ring denoted by formula II where m is an integer from three to eight;

or complete a ring selected from 3-azabicyclo[3.2.2]nonan-3-yl, 2-azabicyclo[2.2.2]octan-2-yl, 3-azabicyclo[3.1.0]hexan-3-yl, or 3-azabicyclo[3.2.0]heptan-3-yl;

$R_3$ and $R_4$ are independently attached to the cyclohexane ring at the 4- or 5-positions, and are independently hydrogen, methoxy, or are points of attachment of a spiro five- or six-membered heterocyclic ring containing one oxygen atom; and A is a saturated carbocyclic ring of from three to six carbon atoms, or is selected from:

formula III where $R_5$ is hydrogen, and $R_6$ and $R_7$ are independently hydrogen, hydroxy, fluorine, chlorine, bromine, trifluoromethyl, methyl or ethyl, and at least one of $R_6$ and $R_7$ is a substituent other than hydrogen;

or formula IV where $R_8$ and $R_9$ are hydrogen;

or formula V where $R_8$ and $R_9$ are hydrogen;

or formula VI where $R_{10}$ is hydrogen, and Z is O, S, or N—$R_{11}$ where $R_{11}$ is hydrogen or methyl;

or formula VII when X is a direct bond;

or formula VIII when X is a direct bond.

In another embodiment, a compound comprises an enantiomer or geometric isomer of a compound of formula XI, or a solvate or pharmaceutically acceptable salt thereof, the compound of the formula:

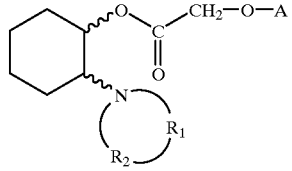

(XI)

wherein $R_1$ and $R_2$, when taken together with the nitrogen atom to which they are attached, form a ring according to formula II where m is an integer from three to eight; and A is selected from:

formula III where $R_5$ is hydrogen, and $R_6$ and $R_7$ are independently hydrogen, hydroxy, amino, fluorine, chlorine, bromine, nitro, trifluoromethyl, methyl, ethyl, methoxy, or ethoxy, and at least one of $R_6$ and $R_7$ is a substituent other than hydrogen;

or formula IV where $R_8$ and $R_9$ are hydrogen;

or formula V where $R_8$ and $R_9$ are hydrogen;

or formula VI where $R_{10}$ is hydrogen, and Z is O or S.

In another embodiment, a compound comprises an enantiomer or geometric isomer of a compound of formula XII, or a solvate or pharmaceutically acceptable salt thereof, the compound of the formula:

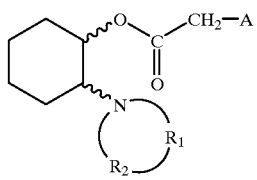

(XII)

wherein $R_1$ and $R_2$, when taken together with the nitrogen atom to which they are attached, form a ring according to formula II where m is an integer from three to eight; and A is selected from:

formula III where $R_5$ is hydrogen, and $R_6$ and $R_7$ are independently hydrogen, hydroxy, amino, fluorine, chlorine, bromine, nitro, trifluoromethyl, methyl, ethyl, methoxy, or ethoxy, and at least one of $R_6$ and $R_7$ is a substituent other than hydrogen;

or formula IV where $R_8$ and $R_9$ are hydrogen;

or formula V where $R_8$ and $R_9$ are hydrogen;

or formula VI where $R_{10}$ is hydrogen, and Z is O or S;

with the proviso that, when $R_1$ and $R_2$ taken together with the nitrogen atom to which they are attached form a pyrrolidinyl ring, A may not be 4-thianaphthenyl.

In another embodiment, a compound comprises an enantiomer or geometric isomer of a compound of formula XIII, or a solvate or pharmaceutically acceptable salt thereof, the compound of the formula:

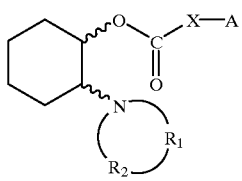

(XIII)

wherein X is a direct bond, trans-CH=CH—, —CH$_2$— or —CH$_2$—O—;

$R_1$ and $R_2$, when taken together with the nitrogen atom to which they are attached, complete a ring selected from pyrrolidinyl, piperidinyl, hexahydroazepinyl, morpholinyl, methylpiperazinyl or 3-azabicyclo[3.2.2]nonanyl; and A is selected from cyclohexyl, 3,4-dichlorophenyl, 4-bromophenyl, 1-naphthyl, 2-naphthyl or 3-thianaphthenyl.

In another embodiment, a compound comprises an enantiomer or geometric isomer of a compound of formula XIV, or a solvate or pharmaceutically acceptable salt thereof, the compound of the formula:

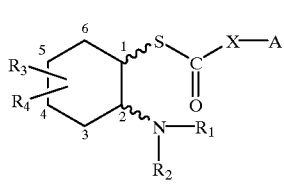

(XIV)

wherein X is a direct bond;

or —(CH$_2$)$_n$—Y—, where n=1, 2, or 3, and Y is a direct bond, O or S;

or —CH(R$_{12}$)—Y—, where R$_{12}$ is alkyl of from one to six carbon atoms, a saturated carbocyclic ring of from three to six carbon atoms, phenyl or benzyl, and Y is a direct bond, O or S;

or —C(R$_{13}$)=CH—, where R$_{13}$ is hydrogen, alkyl of from one to six carbon atoms, or phenyl;

$R_1$ and $R_2$ are independently hydrogen, alkyl of three to eight carbon atoms, alkoxyalkyl of three to eight carbon atoms, or aralkyl of seven to twelve carbon atoms;

or $R_1$ and $R_2$, when taken together with the nitrogen atom to which they are attached, form a ring denoted by formula II:

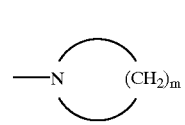

(II)

where m is an integer from three to eight, and the ring may be substituted at any one carbon atom by hydroxy, oxo, alkyl of one to three carbon atoms or alkoxy of one to three carbon atoms, or may be fused at two adjacent carbon atoms with an aromatic or aliphatic carbocyclic ring of six carbon atoms;

or complete a saturated monocyclic nitrogen heterocyclic ring of five to eight ring atoms, containing only carbon, nitrogen and optionally oxygen ring atoms, and the heterocyclic ring containing not more than two nitrogen ring atoms, the second nitrogen being optionally substituted with an alkyl group of one to six carbon atoms or a phenyl ring;

or complete a ring selected from 3-azabicyclo[3.2.2] nonan-3-yl, 2-azabicyclo[2.2.2]octan-2-yl, 3-azabicyclo[3.1.0]hexan-3-yl, or 3-azabicyclo[3.2.0] heptan-3-yl;

$R_3$ and $R_4$ are independently attached to the cyclohexane ring at the 3-, 4-, 5-, or 6-positions, and are independently hydrogen, hydroxy, alkyl of one to six carbon atoms or alkoxy of one to six carbon atoms, or are points of attachment of a spiro five- or six-membered heterocyclic ring containing one oxygen or sulfur atom; and A is an alkyl group of five to twelve carbon atoms, or is a saturated carbocyclic ring of three to six carbon atoms, or is selected from formulae III, IV, V, VI, VII or VIII:

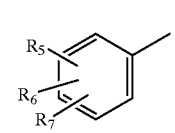

(III)

where $R_5$, $R_6$ and $R_7$ are independently hydrogen, hydroxy, amino, fluorine, chlorine, bromine, nitro, trifluoromethyl, alkyl of one to six carbon atoms, alkoxy of one to six carbon atoms, or aryl, and when X is a direct bond at least one of $R_5$, $R_6$ and $R_7$ is a substituent other than hydrogen;

(IV)

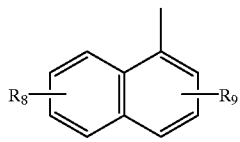

where $R_8$ and $R_9$ are independently hydrogen, hydroxy, fluorine, chlorine, bromine, alkyl of one to six carbon atoms, alkoxy of one to six carbon atoms or aryl;

(V)

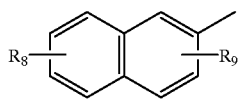

where $R_8$ and $R_9$ are defined as above;

(VI)

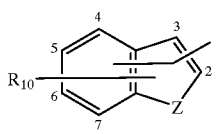

where $R_{10}$ is hydrogen, hydroxy, fluorine, chlorine, bromine, alkyl of from one to six carbon atoms, alkoxy of from one to six carbon atoms, or aryl; Z is $CH_2$, O, S, or $N-R_{11}$ where $R_{11}$ is hydrogen or alkyl of one to six carbon atoms;

(VII)

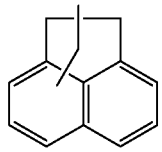

only when X is a direct bond;

(VIII)

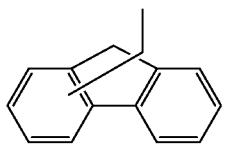

only when X is a direct bond.

In another embodiment, a compound comprises an enantiomer or geometric isomer of a compound of formula XIV, or a solvate or pharmaceutically acceptable salt thereof, the compound of the formula:

(XIV)

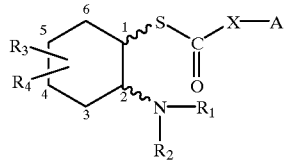

wherein X is a direct bond;
  or $-(CH_2)_n-Y-$, where n=1, and Y is a direct bond, O or S;
  or $-CH(R_{12})-$, where $R_{12}$ is alkyl of from one to six carbon atoms;
  or $-C(R_{13})=CH-$, where $R_{13}$ is hydrogen;
  $R_1$ and $R_2$ are defined as in formula XIV as first described herein;
  $R_3$ and $R_4$ are independently attached to the cyclohexane ring at the 4- or 5-positions, and are independently hydrogen, alkoxy of one to six carbon atoms, or are points of attachment of a spiro five- or six-membered heterocyclic ring containing one oxygen atom; and
  A is defined as in formula XIV as first described herein.

In another embodiment, a compound comprises an enantiomer or geometric isomer of a compound of formula XV, or a solvate or pharmaceutically acceptable salt thereof, the compound of the formula:

(XV)

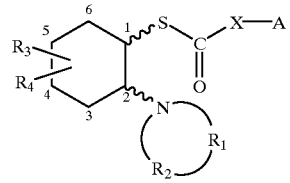

wherein X is a $-CH_2-$ or $-CH_2-O-$;
  $R_1$ and $R_2$, when taken together with the nitrogen atom to which they are attached, form a ring according to formula II, where m is an integer from three to eight, and the ring may be substituted at any one carbon atom by hydroxy, oxo, alkyl of one to three carbon atoms or alkoxy of one to three carbon atoms, or may be fused at two adjacent carbon atoms with an aromatic or aliphatic carbocyclic ring of six carbon atoms;
    or complete a saturated monocyclic nitrogen heterocyclic ring of five to eight ring atoms, containing only carbon, nitrogen and optionally oxygen ring atoms, and the heterocyclic ring containing not more than two nitrogen ring forming atoms, the second nitrogen being optionally substituted with an alkyl group of one to six carbon atoms or a phenyl ring;
    or complete a ring selected from 3-azabicyclo[3.2.2] nonan-3-yl, 2-azabicyclo[2.2.2]octan-2-yl, 3-azabicyclo[3.1.0]hexan-3-yl, or 3-azabicyclo[3.2.0] heptan-3-yl;
  $R_3$ and $R_4$ are independently attached to the cyclohexane ring at the 4- or 5-positions, and are independently hydrogen, methoxy, or are points of attachment of a five-membered oxaspiran ring; and
  A is a saturated carbocyclic ring of from three to six carbon atoms, or is selected from:
    formula III where $R_5$ is hydrogen, and $R_6$ and $R_7$ are independently hydrogen, hydroxy, fluorine, chlorine, bromine, nitro, trifluoromethyl, methyl, ethyl, methoxy, or ethoxy;

or formula IV where $R_8$ and $R_9$ are hydrogen;

or formula V where $R_8$ and $R_9$ are hydrogen;

or formula VI where $R_{10}$ is hydrogen, and Z is $CH_2$, O, S, or N—$R_{11}$ where $R_{11}$ is hydrogen or methyl.

In another embodiment, a compound comprises an enantiomer or geometric isomer of a compound of formula XVI, or a solvate or pharmaceutically acceptable salt thereof, the compound of the formula:

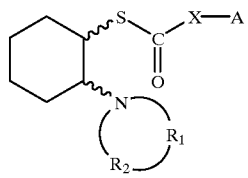

(XVI)

wherein X is a —$CH_2$— or —$CH_2$—O—;

$R_1$ and $R_2$, when taken together with the nitrogen atom to which they are attached, form a ring according to formula II where m is an integer from three to eight; and A is selected from:

formula III where $R_5$ is hydrogen, and $R_6$ and $R_7$ are independently hydrogen, hydroxy, fluorine, chlorine, bromine, nitro, trifluoromethyl, methyl, ethyl, methoxy, or ethoxy;

or formula IV where $R_8$ and $R_9$ are hydrogen;

or formula V where $R_8$ and $R_9$ are hydrogen;

or formula VI where $R_{10}$ is hydrogen, and Z is O or S.

In another aspect of the present invention, compositions are provided that comprise an aminocyclohexyl ester or thioester compound described above in combination with a pharmaceutically acceptable carrier or diluent.

The present invention, in another aspect, provides the compounds described above for use in methods for blocking ion channels in vivo and in vitro. In the in vitro embodiments, the method comprises contacting a preparation containing ion channels with an effective amount of a compound described above. In the in vivo embodiments, the method comprises administering to a warm-blooded animal an effective amount of a compound described above.

In yet another aspect of the present invention, compounds including those described above are provided for the treatment of arrhythmia. In these methods, a compound is administered to a warm-blooded animal in an amount effective to treat arrhythmia.

These and other aspects of the present invention will become evident upon reference to the following detailed description.

DETAILED DESCRIPTION OF THE INVENTION

As noted above, the present invention is directed toward aminocyclohexyl ester and thioester compounds which have a variety of uses. Such uses include blockade of ion channels in vitro and in vivo, and the treatment of arrhythmias.

In one aspect, the compounds of the present invention are esters which may be represented by formula I:

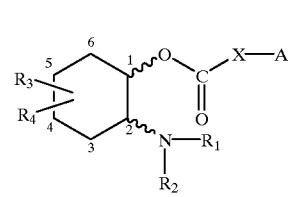

(I)

Compounds of formula I are aminocyclohexyl ester compounds. More specifically, these aminocyclohexyl esters are substituted at position 2 of the cyclohexyl ring with an amino group, $NR_1R_2$. The cyclohexyl ring may also be substituted with additional substituents (designated as $R_3$ and $R_4$) as described in more detail below. Examples of specific embodiments of the elements of compounds represented by formula I include the following.

Depending upon the selection of substituents $R_1$ and $R_2$, the compounds of formula I may be primary, secondary, or tertiary amines (i.e., where $R_1$ and $R_2$ both are hydrogen, or only one is hydrogen, or neither are hydrogen, respectively). Where the amine is tertiary, it may be a cyclic amine. Amino substituents $R_1$ and $R_2$ may be independently selected from substituents which include hydrogen, alkyl groups containing from three to eight carbon atoms, alkoxyalkyl groups containing from three to eight carbon atoms, and aralkyl groups containing from seven to twelve carbon atoms. As used herein, the term "alkyl group" refers to branched or unbranched saturated hydrocarbon fragments containing the specified number of carbon atoms. Examples include n-propyl, isopropyl, and t-butyl. As used herein, the term "alkoxyalkyl" refers to alkyl groups substituted with alkoxy groups which in turn are alkyl groups attached to an oxygen atom. For example, a methoxyethyl group ($CH_3OCH_2CH_2$—) is a three carbon alkoxyalkyl group. As used herein, the term "aralkyl" refers to alkyl groups substituted with aryl groups. Aryl groups are unsubstituted aromatic groups, with phenyl and naphthyl groups preferred. An example of an aralkyl group is the benzyl group ($C_6H_5CH_2$—) which is a seven carbon aralkyl group.

Alternatively, $R_1$ and $R_2$, when taken together with the amino nitrogen atom, may form a ring represented by formula II:

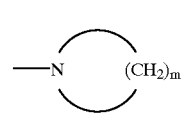

(II)

where m is an integer from three to eight. Additionally, the ring carbon atoms may be also substituted. Suitable substituents include hydroxy, oxo (=O), alkyl groups containing from one to three carbon atoms, and alkoxy groups containing from one to three carbon atoms. The ring may also be fused at two adjacent carbon atoms with a second ring. The second ring may be either an aromatic ring preferably containing either five or six carbon atoms, or an aliphatic carbocycle preferably containing either five or six carbon atoms. Examples of amino substituents containing a fused ring system as described include perhydroindolyl and 1,2,3,4-tetrahydroisoquinolinyl groups.

In addition to $R_1$ and $R_2$ forming a chain of ring carbon atoms, $R_1$ and $R_2$, when taken together with the nitrogen atom to which they are attached, may complete a saturated monocyclic ring of from five to eight ring atoms which includes additional heteroatoms. Preferably, $R_1$ and $R_2$, when taken together, contain only a single heteroatom. Preferred heteroatoms include nitrogen and oxygen. An example of a ring in which $R_1$ and $R_2$ together include oxygen as a ring atom is the morpholinyl group. An example of a ring where $R_1$ and $R_2$ together include nitrogen as a ring atom is the piperazinyl group. For cyclohexyl esters of formula I which are substituted at position 2 with a heterocyclic ring containing two nitrogen ring atoms, the nitrogen of $R_1$ and $R_2$ (i.e., the nitrogen ring atom not attached to the cyclohexyl ring) may be further substituted. Suitable substituents include phenyl and alkyl groups containing from one to six carbon atoms. Examples of such N-phenyl or N-alkyl substitution include N-phenylpiperazinyl and N-methylpiperazinyl, respectively.

Alternatively, $R_1$ and $R_2$, when taken together with the 2-amino nitrogen of formula I, may complete a bicyclic ring. Bicyclic rings include, for example, 3-azabicyclo[3.2.2] nonane, 2-azabicyclo[2.2.2]octane, 3-azabicyclo[3.1.0] hexane, and 3-azabicyclo[3.2.0]heptane. For these derivatives, the 2-substituents of the cyclohexyl esters of formula I are the following groups: 3-azabicyclo[3.2.2] nonan-3-yl, 2-azabicyclo[2.2.2]octan-2-yl, 3-azabicyclo [3.1.0]hexan-3-yl, and 3-azabicyclo[3.2.0]heptan-3-yl.

Cyclohexane substituents $R_3$ and $R_4$ may be independently attached to ring positions 3, 4, 5 or 6 (i.e., both $R_3$ and $R_4$ may be attached to the same ring position or each attached to different ring positions). $R_3$ and $R_4$ are independently selected from substituents which include hydrogen, hydroxy, alkyl groups containing from one to six carbon atoms, alkoxy groups containing from one to six carbon atoms, or points of attachment of a spiro five- or six-membered heterocyclic ring. Preferred heterocyclic substituents contain either a single oxygen or a single sulfur ring atom.

Depending upon the nature of X, the ester side chain, —X—A in formula I above, may take several forms. A compound of formula I may have X as a direct bond. Alternatively, X may be an alkylene moiety, —(CH$_2$)$_n$—, where n=1, 2 or 3, and Y is a direct bond, an oxygen atom, or a sulfur atom; an alkylidene moiety, —CH(R$_{12}$)—Y—, where $R_{12}$ is an alkyl group of from one to six carbon atoms, a saturated carbocyclic ring of from three to six carbon atoms (including cyclopropyl, cyclobutyl, cyclopentyl, and cyclohexyl), a phenyl group, or a benzyl group, and Y is a direct bond, an oxygen atom, or a sulfur atom; or a cis- or trans-alkenyl moiety, —C(R$_{13}$)=CH—, where $R_{13}$ is a hydrogen, an alkyl group of from one to six carbon atoms, or a phenyl group. For compounds of formula I when X is an alkenyl moiety, X is preferably a trans-alkenyl moiety.

Ester side chain component A is generally a hydrophobic moiety. Typically, a hydrophobic moiety is comprised of non-polar chemical groups such as hydrocarbons, hydrocarbons substituted with halogens, and ethers. Suitable hydrocarbons include aliphatic and aromatic hydrocarbons. Preferred aliphatic hydrocarbons include alkyl groups containing from five to twelve carbon atoms and carbocyclic groups containing from three to six carbon atoms. Preferred aromatic groups include phenyl, 1-naphthyl, 2-naphthyl, indenyl (including indene where Z, in formula VI below, is CH$_2$, indole where Z is N—R$_{11}$, benzofuran where Z is O, and thianaphthene where Z is S), acenaphthyl, and fluorenyl derivatives and are represented by formulae III, IV, V, VI, VII or VIII, respectively. As described below, in a preferred embodiment, Z is O, S or N—R$_{11}$, and in a particularly preferred embodiment Z is O or S.

Phenyl groups within the compounds of the present invention are represented by formula III:

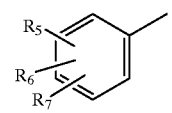

(III)

$R_5$, $R_6$, and $R_7$ are independently selected from substituents which include hydrogen, hydroxy, amino, fluorine, chlorine, bromine, nitro, trifluoromethyl, alkyl groups containing from one to six carbon atoms, alkoxy groups containing from one to six carbon atoms, or aryl groups. For compounds of formula I when X is a direct bond, at least one of $R_5$, $R_6$, and $R_7$ is a hydroxy, fluorine, chlorine, bromine, trifluoromethyl, alkyl of from one to six carbon atoms, or aryl substituent. For compounds of formula I when X is a —CH═CH—, and $R_1$ and $R_2$, when taken together with the nitrogen atom to which they are attached, form a N-phenylpiperazine ring, and $R_3$ and $R_4$ are hydrogen, at least one of $R_5$, $R_6$ and $R_7$ is a substituent other than hydrogen.

1-Naphthyl groups within the compounds of the present invention are represented by formula IV:

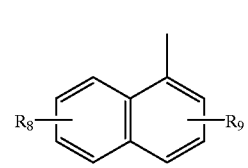

(IV)

$R_8$ and $R_9$ are independently selected from substituents which include hydrogen, hydroxy, fluorine, chlorine, bromine, alkyl groups containing from one to six carbon atoms, alkoxy groups containing from one to six carbon atoms, or aryl groups.

2-Naphthyl groups within the compounds of the present invention are represented by formula V:

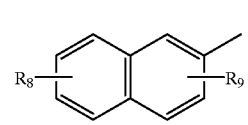

(V)

$R_8$ and $R_9$ are as defined above.

Indenyl groups of the present invention are represented by formula VI:

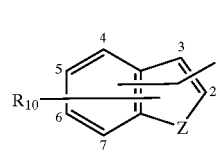

(VI)

$R_{10}$ is selected from substituents which include hydrogen, hydroxy, fluorine, chlorine, bromine, an alkyl group containing from one to six carbon atoms, an alkoxy group containing from one to six carbon atoms, or an aryl group. Z is methylene (CH$_2$), an oxygen atom, sulfur atom, or nitrogen atom bearing a substituent $R_{11}$. The indenyl groups of formula VI are derivatives of indene, indole, benzofuran, and thianaphthene when Z is methylene, nitrogen, oxygen, and sulfur, respectively. Nitrogen substituent $R_{11}$ may be hydrogen or an alkyl group containing from one to six carbon atoms. For compounds of formula I when X is —$(CH_2)_n$—Y—, and n=1, and Y is a direct bond, and $R_1$ and $R_2$, when taken together with the nitrogen atom to which they are attached, form a pyrrolidinyl ring, and $R_3$ and $R_4$ are hydrogen, A may not be 4-thianapthenyl.

Acenaphthyl groups within the compounds of the present invention are represented by formula VII:

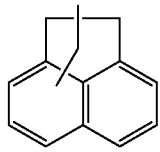

(VII)

Fluorenyl groups within the compounds of the present invention are represented by formula VIII:

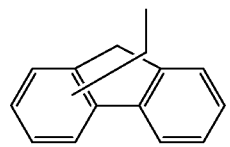

(VIII)

Ester side chain component A may be an acenaphthyl or fluorenyl group only when X is a direct bond. In a preferred embodiment, the acenaphthyl group is a 1-acenaphthyl group, and the fluorenyl group is a 9-fluorenyl group.

As mentioned above, the present invention provides aminocyclohexyl esters represented by formula I. In a preferred embodiment, where X is —$(CH_2)_n$—Y—, n is 1. For these embodiments, Y is a direct bond, an oxygen atom, or a sulfur atom. In a particularly preferred embodiment, Y is a direct bond or an oxygen atom. In a preferred embodiment, where X is —$CH(R_{12})$—, $R_{12}$ is an alkyl group from one to six carbon atoms. In a preferred embodiment, where X is —$C(R_{13})$=CH—, $R_{13}$ is a hydrogen atom. For these embodiments, $R_3$ and $R_4$ are preferably independently attached to the cyclohexane ring at the 4- or 5-positions.

In a preferred embodiment where X is —$(CH_2)_n$—Y—, where n=1 and Y is an oxygen atom, and $R_1$ and $R_2$ are included in a ring, the present invention provides aminocyclohexyl esters represented by formula IX:

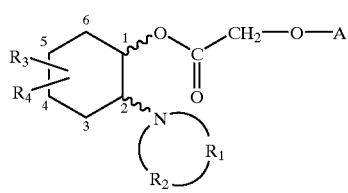

(IX)

In a preferred embodiment where X is —$(CH_2)_n$—Y—, where n=1 and Y is a direct bond, and $R_1$ and $R_2$ are included in a ring as described above, the present invention provides aminocyclohexyl esters represented by formula X:

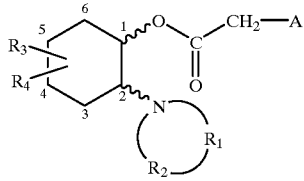

(X)

For either formula IX or X, $R_3$ and $R_4$ are preferably independently attached to the cyclohexane ring at the 4- or 5-positions, and are independently selected from substituents which include hydrogen, methoxy, or are points of attachment of a five-membered oxaspiran ring. Similarly, for either formula IX or X, A is preferably a saturated carbocyclic ring of from three to six carbon atoms, or is selected from: formula III where $R_5$ is hydrogen, and $R_6$ and $R_7$ are independently hydrogen, hydroxy, amino, fluorine, chlorine, bromine, nitro, trifluoromethyl, methyl, ethyl, methoxy, or ethoxy, and at least one of $R_6$ and $R_7$ is a substituent other than hydrogen; or formula IV where $R_8$ and $R_9$ are hydrogen; or formula V where $R_8$ and $R_9$ are hydrogen; or formula VI where $R_{10}$ is hydrogen, and Z is $CH_2$, O, S, or N—$R_{11}$ where $R_{11}$ is hydrogen or methyl. However, for compounds represented by formula X, when $R_1$ and $R_2$, taken together with the nitrogen atom to which they are attached, form a pyrrolidinyl ring, and $R_3$ and $R_4$ are hydrogen, A may not be 4-thianaphthenyl.

In a preferred embodiment where X is a direct bond or —CH=CH—, the present invention provides aminocyclohexyl esters represented by formula I. For these embodiments, $R_1$ and $R_2$ are independently hydrogen, alkyl of three to eight carbon atoms, alkoxyalkyl of three to eight carbon atoms, or aralkyl of seven to twelve carbon atoms; or $R_1$ and $R_2$, when taken together with the nitrogen atom to which they are attached, form a ring denoted by formula II where m is an integer from three to eight; or $R_1$ and $R_2$ complete a ring selected from 3-azabicyclo[3.2.2]nonan-3-yl, 2-azabicyclo[2.2.2]octan-2-yl, 3-azabicyclo[3.1.0]hexan-3-yl, or 3-azabicyclo[3.2.0]heptan-3-yl. $R_3$ and $R_4$ are independently attached to the cyclohexane ring at the 4- or 5-positions, and are independently hydrogen, methoxy, or points of attachment of a spiro five- or six-membered heterocyclic ring containing one oxygen atom. A is a saturated carbocyclic ring of from three to six carbon atoms or is selected from: formula III where $R_5$ is hydrogen, and $R_6$ and $R_7$ are independently hydrogen, hydroxy, fluorine, chlorine, bromine, trifluoromethyl, methyl, and ethyl, and at least one of $R_6$ and $R_7$ is a substituent other than hydrogen; or formula IV where $R_8$ and $R_9$ are hydrogen; or formula V where $R_8$ and $R_9$ are hydrogen; or formula VI where $R_{10}$ is hydrogen, and Z is O, S, or N—$R_{11}$ where $R_{11}$ is hydrogen or methyl; or formula VII when X is a direct bond; or formula VIII when X is a direct bond.

In a preferred embodiment where X is —$(CH_2)_n$—Y—, where n=1 and Y is an oxygen atom, $R_1$ and $R_2$ are included in a ring, and there are no $R_3$ and $R_4$, the present invention provides aminocyclohexyl esters represented by formula XI:

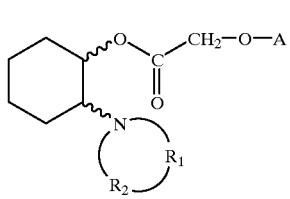

(XI)

In a preferred embodiment where X is —$(CH_2)_n$—Y—, where n=1 and Y is a direct bond, $R_1$ and $R_2$ are included in a ring, and there are no $R_3$ and $R_4$, the present invention provides aminocyclohexyl esters represented by formula XII:

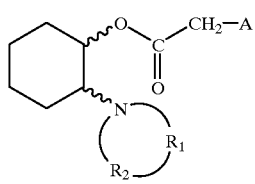

(XII)

For either formula XI and XII, $R_1$ and $R_2$ preferably are taken together with the nitrogen atom to which they are attached to form a ring according to formula II where m is an integer from three to eight. Similarly, for either formula XI or XII, A is preferably selected from: formula III where $R_5$ is hydrogen, and $R_6$ and $R_7$ are independently hydrogen, hydroxy, amino, fluorine, chlorine, bromine, nitro, trifluoromethyl, methyl, ethyl, methoxy, or ethoxy, and at least one of $R_6$ and $R_7$ is a substituent other than hydrogen; or formula IV where $R_8$ and $R_9$ are hydrogen; or formula V where $R_8$ and $R_9$ are hydrogen; or formula VI where $R_{10}$ is hydrogen, and Z is O or S.

In a preferred embodiment where X is selected from a direct bond; trans-$C(R_{13})$=CH— where $R_{13}$ is a hydrogen atom; or —$(CH_2)_n$—Y— where n=1 and Y is a direct bond or an oxygen atom, $R_1$ and $R_2$ are included in a ring, and there are no $R_3$ and $R_4$, the present invention provides aminocyclohexyl esters represented by formula XIII:

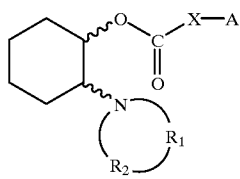

(XIII)

$R_1$ and $R_2$, when taken together with the nitrogen atom to which they are attached, complete a ring selected from pyrrolidinyl, piperidinyl, hexahydroazepinyl, morpholinyl, methylpiperazinyl or 3-azabicyclo[3.2.2]nonanyl. A is preferably selected from 3,4-dichlorophenyl, 1-naphthyl, 2-naphthyl, cyclohexyl, 4-bromophenyl, or 3-thianaphthenyl. In a preferred embodiment, the stereochemistry is the trans-configuration. In another preferred embodiment, the stereochemistry is the cis-configuration.

In another aspect, the compounds of the present invention are aminocyclohexyl thioesters which may be represented by formula XIV:

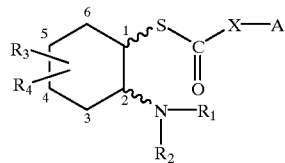

(XIV)

X, $R_1$, $R_2$, $R_3$, $R_4$ and A are defined as for formula I as first described herein, except that where X is —$(CH_2)_n$—Y—, and n=1, and Y is a direct bond, and $R_1$ and $R_2$, when taken together with the nitrogen atom to which they are attached, form a pyrrolidinyl ring, and $R_3$ and $R_4$ are hydrogen, A may be 4-thianaphthenyl.

In a preferred embodiment where X is selected from a direct bond; —$(CH_2)_n$—Y— where n=1, and Y is a direct bond, an oxygen atom, or a sulfur atom; or —$CH(R_{12})$— where $R_{12}$ is an alkyl group of from one to six carbon atoms; or —$C(R_{13})$=CH— where $R_{13}$ is hydrogen; the present invention provides aminocyclohexyl thioesters represented by formula XIV.

$R_3$ and $R_4$ are independently attached to the cyclohexane ring at the 4- or 5-positions, and are independently hydrogen, alkoxy of from one to six carbon atoms, or are points of attachment of a spiro five- or six-membered heterocyclic ring containing one oxygen atom. A is preferably an alkyl group of five to twelve carbon atoms, or is a saturated carbocyclic ring of from three to six carbon atoms, or is preferably selected from: formula III where $R_5$, $R_6$, and $R_7$ are independently hydrogen, hydroxy, amino, fluorine, chlorine, bromine, nitro, trifluoromethyl, alkyl of from one to six carbon atoms, alkoxy of from one to six carbon atoms, or aryl, and when X is a direct bond at least one of $R_5$, $R_6$ and $R_7$ is a substituent other than hydrogen; or formula IV where $R_8$ and $R_9$ are independently hydrogen, hydroxy, fluorine, chlorine, bromine, alkyl of one to six carbon atoms, alkoxy of one to six carbon atoms, or aryl; or formula V where $R_8$ and $R_9$ are independently hydrogen, hydroxy, fluorine, chlorine, bromine, alkyl of one to six carbon atoms, alkoxy of one to six carbon atoms, or aryl; or formula VI where $R_{10}$ is independently hydrogen, hydroxy, fluorine, chlorine, bromine, alkyl of one to six carbon atoms, alkoxy of one to six carbon atoms, or aryl; and Z is $CH_2$, O, S, or N—$R_{11}$ where $R_{11}$ is hydrogen or alkyl of one to six carbon atoms; or formula VII when X is a direct bond; a formula VIII when X is a direct bond.

In a preferred embodiment, where X is a —$(CH_2)_n$—Y—, and n=1, and Y is a direct bond or an oxygen atom, and $R_1$ and $R_2$ are included in a ring, the present invention provides aminocyclohexyl thioesters represented by formula XV.

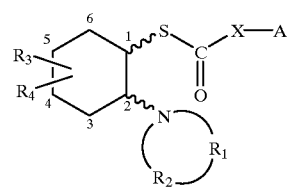

(XV)

$R_1$ and $R_2$ are preferably taken together with the nitrogen atom to which they are attached to form a ring according to formula II, where m is an integer from three to eight, and the ring may be substituted at any one carbon atom by hydroxy, oxo, alkyl of one to three carbon atoms or alkoxy of one to three carbon atoms, or may be fused at two adjacent carbon atoms with an aromatic or aliphatic carbocyclic ring of five to six carbon atoms; or complete a saturated monocyclic nitrogen heterocyclic ring of five to eight ring atoms, containing only carbon, nitrogen and optionally oxygen ring atoms, and the heterocyclic ring containing not more than two nitrogen ring forming atoms, wherein the second nitrogen is optionally substituted with an alkyl group of one to six carbon atoms or a phenyl ring; or complete a ring selected from 3-azabicyclo[3.2.2]nonan-3-yl, 2-azabicyclo[2.2.2] octan-2-yl, 3-azabicyclo[3.1.0]hexan-3-yl, or 3-azabicyclo [3.2.0]heptan-3-yl. $R_3$ and $R_4$ are independently attached to the cyclohexane ring at the 4- or 5-positions, and are independently hydrogen, methoxy, or are points of attachment of a five-membered oxaspiran ring. A is preferably a saturated carbocyclic ring of from three to six carbon atoms, or is preferably selected from: formula III where $R_5$ is hydrogen, and $R_6$ and $R_7$ are independently hydrogen, hydroxy, fluorine, chlorine, bromine, nitro, trifluoromethyl, methyl, ethyl, methoxy, or ethoxy; or formula IV where $R_8$ and $R_9$ are hydrogen; or formula V where $R_8$ and $R_9$ are hydrogen; or formula VI where $R_{10}$ is hydrogen, and Z is $CH_2$, O, S, or N—$R_{11}$ where $R_{11}$ is hydrogen or methyl.

In a preferred embodiment where X is —$(CH_2)_n$—Y—, and n=1, and Y is a direct bond or an oxygen atom, $R_1$ and $R_2$ are included in a ring, and there are no $R_3$ and $R_4$, the present invention provides aminocyclohexyl thioesters represented by formula XVI:

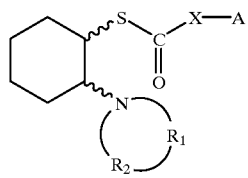

(XVI)

$R_1$ and $R_2$ are preferably taken together with the nitrogen atom to which they are attached to form a ring according to formula II where m is an integer from three to eight. A is preferably selected from: formula III where $R_5$ is hydrogen, and $R_6$ and $R_7$ are independently hydrogen, hydroxy, fluorine, chlorine, bromine, nitro, trifluoromethyl, methyl, ethyl, methoxy, or ethoxy; or formula IV where $R_8$ and $R_9$ are hydrogen; or formula V where $R_8$ and $R_9$ are hydrogen; or formula VI where $R_{10}$ is hydrogen, and Z is O or S.

In the formulae depicted above, a bond to a substituent and/or a bond that links A with the remainder of a compound may be shown as intersecting one or more bonds in a ring structure. This indicates that the substituent may be attached at any one of the carbon atoms in the ring structure.

The wavy line bonds in the above formulae indicate that the substituents at positions 1 and 2 of the cyclohexane ring may be disposed in a cis or trans relationship. The substituents $R_3$ and $R_4$ may also be independently attached cis or trans to the 2-amino substituent. The compounds of the present invention contain at least two asymmetric carbon atoms and thus exist as enantiomers and diastereomers. Unless otherwise noted, the present invention includes all enantiomeric and diastereomeric forms of the compounds of the above formulae. Pure stereoisomers, mixtures of enantiomers and/or diastereomers, and mixtures of different compounds of the above formulae are included within the present invention.

The compounds of the above formulae may be prepared using known synthetic methodology. In general, compounds of the present invention are prepared by reacting the appropriate 1,2-aminocyclohexanol or 1,2-aminocyclohexanethiol with an appropriate carboxylic acid derivative, derived from A—X—COOH. The carboxylic acid may be converted to a reactive intermediate such as the acid chloride by treatment with, for example, thionyl chloride. The reaction between the acid chloride and the alcohol or thiol is carried out in a suitable solvent, such as chloroform. The reaction temperature may be dependent upon the nature of the reactants, however, in general, the reaction may be refluxed. When the reaction has proceeded to substantial completion, the desired product is recovered from the reaction mixture by conventional organic chemistry techniques, and is purified generally by recrystallisation. This reaction sequence as described generates the aminocyclohexylester as the hydrochloride salt, unless an acid scavenger such as triethylamine is added to the mixture, in which case the product is the free base. The hydrochloride may be converted, if desired, to the free base form by known methodologies, and subsequently, if desired, to other acid addition salts by reaction with inorganic or organic acids. Acid addition salts can also be prepared metathetically by reacting one acid addition salt with an acid which is stronger than that of the anion of the initial salt.

Alternative routes based on known methodologies, such as those described below, may be used to prepare the aminocyclohexylester compounds of the present invention. The carboxylic acid may be converted to an alternative reactive derivative such as an activated ester, anhydride or acyl imidazole and reacted with the appropriate 1,2-aminocyclohexanol or 1,2-aminocyclohexanethiol. The carboxylic acid may be reacted directly with the aminoalcohol or aminothiol with the aid of a coupling reagent such as dicyclohexylcarbodiimide. The starting 1,2-aminocyclohexanol or 1,2-aminocyclohexanethiol compounds are prepared by reaction sequences well known in the art. For example, trans-1,2-aminocyclohexanols are commonly prepared by the ring-opening reaction of cyclohexene oxide with the appropriate amine. The starting carboxylic acids are known or are prepared by reaction sequences well known in the art.

The synthesis procedures described herein, especially when taken with the general knowledge in the art, provide sufficient guidance to those of ordinary skill in the art to perform the synthesis, isolation, and purification of the preferred compounds described herein and other analogous compounds. Individual enantiomers may be obtained, if desired, from mixtures of the different forms by known methods of resolution, such as the formation of diastereomers, followed by recrystallisation.

The compounds of the above formulae may be in the form of a solvate or a pharmaceutically acceptable salt, e.g., an acid addition salt. Such salts include hydrochloride, sulfate, phosphate, citrate, fumarate, methanesulfonate, acetate, tartrate, maleate, lactate, mandelate, salicylate, succinate and other salts known in the art.

A compound of the present invention may be prepared as a composition by combining it with a pharmaceutically acceptable carrier or diluent. Suitable carriers or diluents include physiological saline. It will be evident to those of ordinary skill in the art that a composition of the present invention may contain more than one aminocyclohexyl ester and/or thioester compound.

As noted above, the present invention provides for utilizing the compounds described above in in vitro and in vivo methods. In one aspect, ion channels, such as cardiac sodium channels, are blocked in vitro or in vivo. A preparation that contains ion channels is contacted with, or a warm-blooded animal is administered, an effective amount of an aminocyclohexyl ester and/or thioester compound. Suitable preparations containing cardiac sodium channels include cells isolated from cardiac tissue as well as cultured cell lines. The step of contacting includes, for example, incubation of ion channels with a compound under conditions and for a time sufficient to permit blockage of the channels by the compound.

In another aspect, the compounds described above are provided for treating arrhythmia. As used herein, "treating arrhythmia" refers to both therapy for arrhythmia and for the prevention of arrhythmias occurring in a heart that is susceptible to arrhythmia. An effective amount of a compound or composition of the present invention is used to treat arrhythmia in a warm-blooded animal, such as a human. Methods of administering effective amounts of antiarrhythmic agents are well known in the art and include the administration of an oral or parenteral dosage form. Such dosage forms include, but are not limited to, parenteral solutions, tablets, capsules, sustained release implants, and transdermal delivery systems. Generally, oral or intravenous administration is preferred. The dosage amount and frequency are selected to create an effective level of the agent without harmful effects. It will generally range from a dosage of from about 0.1 to about 100 mg/kg/day, and typically from about 0.1 to 10 mg/kg where administered orally or intravenously for antiarrhythmic effect.

Administration of compounds or compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity.

In order to assess whether a compound has a desired pharmacological activity within the present invention, it is subjected to a series of tests. In the first of such tests, a compound is given as increasing (doubling with each dose) intravenous boluses every 8 minutes to a pentobarbital anesthetized rat. The effects of the compound on blood pressure, heart rate and the ECG are measured 30 seconds, 1, 2, 4 and 8 minutes after each dose. Increasing doses are given until the animal dies. The cause of death is identified as being of either respiratory or cardiac origin. This test gives an indication as to whether the compound is blocking sodium channels and/or potassium channels, and in addition gives information about acute toxicity. The indices of sodium channel blockade are increasing P-R interval and QRS widening of the ECG. Potassium channel blockade results in Q-T interval prolongation of the ECG.

A second test involves administration of a compound as an infusion to pentobarbital anesthetized rats in which the left ventricle is subjected to electrical square wave stimulation performed according to a preset protocol described in further detail below. This protocol includes the determination of thresholds for induction of extrasystoles and ventricular fibrillation. In addition, effects on electrical refractoriness are assessed by a single extra beat technique. In addition effects on blood pressure, heart rate and the ECG are recorded. In this test, sodium channel blockers produce the ECG changes expected from the first test. In addition, sodium channel blockers also raise the thresholds for induction of extrasystoles and ventricular fibrillation. Potassium channel blockade is revealed by increasing refractoriness and widening of the Q-T intervals of the ECG.

A third test involves exposing isolated rat hearts to increasing concentrations of a compound. Ventricular pressures, heart rate, conduction velocity and ECG are recorded in the isolated heart in the presence of varying concentrations of the compound. This test provides evidence for direct toxic effects on the myocardium. Additionally, selectivity, potency and efficacy of action of a compound can be ascertained under conditions simulating ischaemia. Concentrations found to be effective in this test are expected to be efficacious in the electrophysiological studies.

A fourth test is estimation of the antiarrhythmic activity of a compound against the arrhythmias induced by coronary artery occlusion in anaesthetized rats. It is expected that a good antiarrhythmic compound will have antiarrhythmic activity at doses which have minimal effects on either the ECG, blood pressure or heart rate under normal conditions.

A compound is also tested directly for effects on sodium and potassium currents in isolated rat myocytes. Isolated rat myocytes are obtained in the conventional manner from isolated hearts. They are used in voltage clamp studies. In order to obtain adequate voltage clamps for estimation of a compound's effects on sodium and potassium currents, the whole-cell patch clamp technique is used. In this technique, a microelectrode is attached to a cell in such a manner that the cell's internal contents are in free communication with the electrode's content. Using the appropriate buffers and conventional voltage step protocols, both sodium and potassium currents can be identified. The activity of a compound is tested on these currents.

All of the foregoing tests are performed using rat tissue. In order to ensure that a compound is not having effects which are only specific to rat tissue, further experiments are performed in dogs and primates. In order to assess possible sodium channel and potassium channel blocking actions in vivo in dogs, a compound is tested for effects on the ECG, ventricular epicardial conduction velocity and responses to electrical stimulation. An anesthetized dog is subjected to an open chest procedure to expose the left ventricular epicardium. After the pericardium is removed from the heart a recording/stimulation electrode is sewn onto the epicardial surface of the left ventricle. Using this array, and suitable stimulation protocols, conduction velocity across the epicardium as well as responsiveness to electrical stimulation can be assessed. This information coupled with measurements of the ECG allows one to assess whether sodium and/or potassium channel blockade occurs. As in the first test in rats, a compound is given as a series of increasing bolus doses. At the same time possible toxic effects of a compound on the dog's cardiovascular system is assessed.

The effects of a compound on the ECG and responses to electrical stimulation are also assessed in intact, halothane anesthetized baboons (Papio anubis). In this preparation, a blood pressure cannula and ECG electrodes are suitably placed in an anesthetized baboon. In addition, a stimulating electrode is placed into the right ventricle, together with a monophasic action potential electrode. As in the tests described above, ECG and electrical stimulation responses to a compound reveal the possible presence of sodium and/or potassium channel blockade. The monophasic action potential also reveals whether a compound widens the action potential, an action expected of a potassium channel blocker.

The present invention also provides kits that contain a pharmaceutical composition which includes one or more compounds of the above formulae. The kit also includes instructions for the use of the pharmaceutical composition for the blocking of ion channels or for the treatment of arrhythmia. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

The following examples are offered by way of illustration and not by way of limitation.

EXAMPLES

Example 1

(±)-trans-[2-(1-pyrrolidinyl)cyclohexyl](3,4-dichlorophenoxy)acetate monohydrochloride (Compound #1)

(i) Pyrrolidine (10.5 g, 148 mmol), cyclohexene oxide (15 mL, 148 mmol) and water (5 mL) are refluxed under nitrogen until GC or tlc analysis shows the reaction to be complete. The cooled mixture is partitioned between saturated sodium hydroxide solution (150 mL) and ether (150 mL). The aqueous layer is washed with additional ether (75 mL) and the combined ether layers are dried over sodium sulfate. The ether is removed in vacuo to leave the crude aminoalcohol (26 g), which is vacuum distilled (bp 51° C. at full vacuum) to give (±)-trans-[2-(1-pyrrolidinyl)] cyclohexanol.

(ii) 3,4-Dichlorophenoxyacetic acid (2.62 g, 12 mmol) is refluxed in thionyl chloride (10 mL) under nitrogen for 1 hour. After stirring at room temperature for a further hour, the thionyl chloride is removed in vacuo to leave an orange oil, which is dissolved in chloroform (10 mL). The acid chloride solution is refluxed for 12 hours with a solution of (±)-trans-[2-(1-pyrrolidinyl)]cyclohexanol (2 g, 12 mmol) in chloroform (5 mL) under nitrogen. Ether (40 mL) is added to the cooled mixture, the mixture is stirred for 30 min., and the crude product is filtered off (3.61 g) and washed with ether. It is recrystallised from the minimum volume of hot methanol/ether to yield the title compound.

Example 2

(±)-trans-[2-(1-pyrrolidinyl)cyclohexyl](1-naphthoxy)acetate monohydrochloride (Compound #2)

The title compound is prepared according to the method described in Example 1(ii), using 1-naphthoxyacetic acid (2.4 g, 12 mmol) to prepare the acid chloride as a yellow solid, which is dissolved in chloroform (25 mL). This solution is added to a solution of (±)-trans-[2-(1-pyrrolidinyl)]cyclohexanol prepared as in Example 1(i) (2 g, 12 mmol) in chloroform (5 mL) under nitrogen. The mixture is refluxed for 10 hours. All solvent is removed in vacuo. The resulting solid is mixed with hot ethyl acetate (100 mL) and methanol is added until it dissolves. On cooling, the solid is collected and washed with ethyl acetate, and recrystallised from hot methanol/ethyl acetate to give the title compound.

Example 3

(±)-trans-{2-[N-(3-azabicyclo[3.2.2]nonyl)] cyclohexyl}(3,4-dichlorophenoxy)acetate monohydrochloride (Compound #3)

(i) (±)-trans-{2-[N-(3-Azabicyclo[3.2.2]nonyl)]} cyclohexanol is prepared according to the method described in Example 1(i) by refluxing 3-azabicyclo[3.2.2] nonane (5 g, 40 mmol), cyclohexene oxide (3.9 mL, 40 mmol) and water (3 mL) for 5 hours. The crude product, a waxy yellowish solid obtained on removal of ether, is used without further purification.

(ii) A chloroform solution (15 mL) of 3,4-dichlorophenoxyacetyl chloride, prepared from 3,4-dichlorophenoxyacetic acid (2 g, 9 mmol) as in Example 1(ii), is added to a solution of (±)-trans-{2-[N-(3-azabicyclo [3.2.2]nonyl)]}cyclohexanol (2 g, 9 mmol) in chloroform (7 mL) under nitrogen. The mixture is refluxed for 12 hours. Ether (30 mL) is added to the cooled mixture, and the crude product is filtered off and washed with ether. It is recrystallised from the minimum volume of hot ethyl acetate to yield the title compound.

Example 4

(±)-trans-[2-(4-morpholinyl)cyclohexyl](3,4-dichlorophenoxy)acetate monohydrochloride (Compound #4)

(i) (±)-trans-[2-(4-Morpholinyl)]cyclohexanol is prepared by the method detailed in Example 1(i), refluxing morpholine (5 g, 57 mmol), cyclohexene oxide (5.8 mL, 57 mmol) and water (3 mL) for 2 hours. The crude product is purified by full vacuum distillation (bp 75–80° C.).

(ii) A chloroform solution (10 mL) of 3,4-dichlorophenoxyacetyl chloride, prepared from 3,4-dichlorophenoxyacetic acid (2.4 g, 11 mmol) as in Example 1(ii), is added to a solution of (±)-trans-[2-(4-morpholinyl)] cyclohexanol (2 g, 11 mmol) in chloroform (5 mL) under nitrogen. The mixture is refluxed for 8 hours. The crude product is filtered off and washed with ether. More ether may be added to the filtrate to yield further crude product. The product is recrystallised from hot methanol to give the title compound.

Example 5

(±)-trans-[2-(1-hexahydroazepinyl)cyclohexyl](3,4-dichlorophenoxy)acetate monohydrochloride (Compound #5)

(i) (±)-trans-[2-(1-Hexahydroazepinyl)]cyclohexanol is prepared by the method detailed in Example 1(i), refluxing hexamethyleneimine (17.3 mL, 0.15 mol), cyclohexene oxide (15.5 mL, 0.15 mol) and water (5 mL). The product is purified by full vacuum distillation (bp 62–65° C.).

(ii) A chloroform solution (10 mL) of 3,4-dichlorophenoxyacetyl chloride, prepared from 3,4-dichlorophenoxyacetic acid (2.36 g, 11 mmol) as in Example 1(ii), is added to a solution of (±)-trans-[2-(1-hexahydroazepinyl)]cyclohexanol (2 g, 10 mmol) in chloroform (5 mL) under nitrogen. The mixture is refluxed for 10 hours. The crude product which precipitates on adding ether to the mixture, is filtered off and washed with ether. It is recrystallised from hot methanol (4 mL), and washed with ether, to give the title compound.

Example 6

(±)-trans-[2-(4-morpholinyl)cyclohexyl]benzo[b] thiophene-3-acetate monohydrochloride (Compound #6)

3-Thianaphtheneacetic acid (4.81 g, 25 mmol) is refluxed in thionyl chloride (16 mL) under nitrogen for 1 hour. After stirring at room temperature for a further 20 min., the thionyl chloride is removed in vacuo to leave a brown oil, which is dissolved in chloroform (10 mL). The acid chloride solution is added to a solution of (±)-trans-[2-(4-morpholinyl)] cyclohexanol prepared as in Example 4(i) (4.5 g, 24.3 mmol) in chloroform (5 mL) under nitrogen. The mixture is refluxed for 11 hours. Ether (25 mL) is added to the cooled mixture and the crude product is filtered off and washed with ether (3×10 mL). The product may be recrystallised from hot methanol/ether to give the title compound.

Example 7

(±)-trans-[2-(1-pyrrolidinyl)cyclohexyl](cyclohexyl) acetate monohydrochloride (Compound #7)

The title compound is prepared according to the method described in Example 1(ii), using cyclohexylacetic acid (4.4 g, 31 mmol) to prepare the acid chloride as a pale yellow oil, which is dissolved in chloroform (10 mL). This solution is added to a solution of (±)-trans-[2-(1-pyrrolidinyl)] cyclohexanol prepared as in Example 1(i) (5 g, 30 mmol) in chloroform (10 mL) under nitrogen. The mixture is refluxed for 15 hours. The solvent is removed in vacuo to leave a solid. The crude product may be recrystallised from hot ethyl acetate or methanol/diethyl ether to give the title compound.

Example 8

(±)-trans-[2-(4-morpholinyl)cyclohexyl]naphthyl-1-acetate monohydrochloride (Compound #8)

1-Naphthylacetic acid (5.30 g, 28.5 mmol) is refluxed in thionyl chloride (10 mL) under nitrogen for 1 hour. After stirring at room temperature for a further 90 min., the thionyl chloride is removed in vacuo to leave an orange-brown oil, which is dissolved in chloroform (10 mL). The acid chloride solution is slowly added to a solution of (±)-trans-[2-(4-morpholinyl)]cyclohexanol prepared as in Example 4(i) (5.0 g, 27 mmol) in chloroform (15 mL) under nitrogen. The mixture is refluxed for 5 hours. The solvent is removed in vacuo, and the residue is partitioned between 1M hydrochloric acid (150 mL) and ether (100 mL). The ether layer is separated and the aqueous is washed with more ether (2×50 mL), and then basified by the addition of 50% sodium hydroxide solution. This is then extracted with ether (3×50 mL), and the combined ether extracts are washed with water until GC shows no unreacted aminoalcohol in the ether. The ether containing the product is then dried over sodium sulfate, and the solvent is removed to leave the crude free ester. The residue is dissolved in ether (40 mL) and dichloromethane (5 mL) and treated with HCl in ether to precipitate the salt. It is washed with ether and recrystallised from ethyl acetate/methanol to yield the title compound.

Example 9

(±)-trans-[2-(4-morpholinyl)cyclohexyl]naphthyl-2-acetate monohydrochloride (Compound #9)

2-Naphthylacetyl chloride is prepared according to the method described in Example 8 using 2-naphthylacetic acid (2.64 g, 14.2 mmol) to give the corresponding acid chloride as a yellow solid which is dissolved in chloroform (10 mL). The solution is refluxed for 9 hours with a solution of (±)-trans-[2-(4-morpholinyl)]cyclohexanol (2.5 g, 13.5 mmol) in chloroform (10 mL) under nitrogen. The solvent is removed in vacuo, and the residue is partitioned between 1M sodium hydroxide solution (100 mL) and dichloromethane (80 mL). The organic layer is separated and the aqueous is washed with more dichloromethane (2×75 mL). The combined dichloromethane extracts are dried over sodium sulfate, and the solvent is removed to leave the crude free ester. This may be purified by column chromatography using silica gel and chloroform/ethyl acetate (3:1) as eluent. The free ester is converted to the salt by treatment with HCl in ether/dichloromethane (3:1). The resulting solid is washed with ether and recrystallised from hot methanol to yield the title compound.

Example 10

(±)-trans-[2-(4-morpholinyl)cyclohexyl] phenylacetate monohydrochloride (Compound #10)

Phenylacetyl chloride is prepared according to the method described in Example 8 using phenylacetic acid (2.13 g, 15.6 mmol) to give a pale yellow oil which is dissolved in chloroform (10 mL). This solution is refluxed for 12 hours with a solution of (±)-trans-[2-(4-morpholinyl)] cyclohexanol (2.75 g, 14.9 mmol) in chloroform (10 mL) under nitrogen. The reaction mixture is partitioned between 1M sodium hydroxide solution (100 mL) and dichloromethane (80 mL). The organic layer is separated and the aqueous is washed with more dichloromethane (2×50 mL). The combined dichloromethane extracts are dried over sodium sulfate, and the solvent is removed to leave the crude free ester. This is purified by column chromatography and converted to the hydrochloride salt as described in Example 9. The product is recrystallised from hot methanol to yield the title compound.

Example 11

(±)-trans-[2-(4-morpholinyl)cyclohexyl](3,4-dichlorophenyl)acetate monohydrochloride (Compound #11)

3,4-Dichlorophenylacetyl chloride is prepared according to the method described in Example 8, using 3,4-dichlorophenylacetic acid (2.62 g, 12.8 mmol) to give a yellow oil which is dissolved in chloroform (15 mL). This solution is refluxed for 9 hours with a solution of (±)-trans-[2-(4-morpholinyl)]cyclohexanol (2.25 g, 12.2 mmol) in chloroform (10 mL) under nitrogen. The solvent is removed in vacuo, and the residue is partitioned between 1M hydrochloric acid (75 mL) and ether (75 mL). The ether layer is separated and the aqueous is washed with more ether (2×30 mL), and then basified to pH14 by the addition of 50% sodium hydroxide solution. This is then extracted with ether (4×30 mL), and the combined ether extracts are washed with water until GC shows no unreacted aminoalcohol in the ether. The ether containing the product is then dried over sodium sulfate, and the solvent is removed to leave the crude free ester. The residue is dissolved in ether (20 mL) and treated with HCl in ether to precipitate the salt. It is washed with ether and recrystallised from hot methanol to yield the title compound.

Example 12

(±)-trans-[2-(4-morpholinyl)cyclohexyl](4-nitrophenyl)acetate monohydrochloride (Compound #12)

4-Nitrophenylacetyl chloride, prepared according to the method described in Example 8 using 4-nitrophenylacetic acid (5.4 g, 29.8 mmol), is dissolved in chloroform (15 mL).

This solution is refluxed for 9 hours with a solution of (±)-trans-[2-(4-morpholinyl)]cyclohexanol (5.25 g, 28.3 mmol) in chloroform (15 mL) under nitrogen. The solvent is removed in vacuo, and the residue is partitioned between 1M hydrochloric acid (60 mL) and ether (50 mL). The ether layer is separated and the aqueous layer is washed with more ether (2×50 mL), and then basified by the addition of 50% sodium hydroxide solution. This is then extracted with ether (5×60 mL), and the combined ether extracts are washed repeatedly with water to remove any unreacted aminoalcohol. The ether containing the product is then dried over sodium sulfate, and the solvent is removed to leave the crude free ester. The residue is dissolved in ether (20 mL) and treated with HCl in ether to precipitate the salt. It is washed with ether and recrystallised from hot methanol to yield the title compound.

Example 13

(±)-trans-[2-(4-methyl-1-piperazinyl)cyclohexyl] naphthyl-2-acetate dihydrochloride (Compound #13)

(i) (±)-trans-[2-(4-Methyl-1-piperazinyl)]cyclohexanol is prepared by the method detailed in Example 1(i), refluxing 1-methylpiperazine (16.6 mL, 150 mmol), cyclohexene oxide (15.2 mL, 150 mmol) and water (5 mL) for 5 hours. The crude product is purified by full vacuum distillation (bp 94° C.) to give a white solid.

(ii) 2-Naphthylacetyl chloride is prepared according to the method described in Example 8 using 2-naphthylacetic acid (2.47 g, 13.3 mmol) to give a yellow solid which is dissolved in chloroform (15 mL). This solution is added to a solution of (±)-trans-[2-(4-methyl-1-piperazinyl)]cyclohexanol (2.5 g, 12.6 mmol) in chloroform (10 mL), and the mixture is refluxed for 11 hours under nitrogen. The solvent is removed in vacuo, and the residue is partitioned between 1M hydrochloric acid (100 mL) and ether (60 mL). The ether layer is separated and the aqueous is washed with more ether (2×30 mL), and then basified by the addition of 50% sodium hydroxide solution. This is then extracted with ether (4×30 mL), and the combined ether extracts are washed repeatedly with water to remove any unreacted aminoalcohol. The ether containing the product is then dried over sodium sulfate, and the solvent is removed to leave the crude free ester. The free ester is dissolved in ether/dichloromethane (35 mL, 4:3) and converted to the dihydrochloride salt by treatment with an excess of HCl in the same solvent. The resulting solid is washed with ether and recrystallised from hot methanol to yield the title compound.

Example 14

(±)-trans-[2-(4-methyl-1-piperazinyl)cyclohexyl] naphthyl-1-acetate monohydrochloride (Compound #14)

1-Naphthylacetyl chloride is prepared according to the method described in Example 8 using 1-naphthylacetic acid (2.47 g, 13.3 mmol) to give a yellow oil which is dissolved in chloroform (10 mL). This solution is added to a solution of (±)-trans-[2-(4-methyl-1-piperazinyl)]cyclohexanol (2.5 g, 12.6 mmol) in chloroform (10 mL), and the mixture is refluxed for 11 hours under nitrogen. The crude free ester is isolated as described in Example 13, and is converted to the monohydrochloride salt in ether/dichloromethane (35 mL, 6:1) by treatment with 1 equivalent of HCl in the same solvent. The resulting solid is washed with ether and recrystallised from hot ethyl acetate/methanol to yield the title compound.

Example 15

(±)-trans-[2-(4-morpholinyl)cyclohexyl]-1-naphthoate monohydrochloride (Compound #15)

1-Naphthoyl chloride, prepared according to the method described in Example 8 using 1-naphthoic acid (2.44 g, 14.2 mmol), is dissolved in chloroform (15 mL). This solution is refluxed for 60 hours with a solution of (±)-trans-[2-(4-morpholinyl)]cyclohexanol (2.5 g, 13.5 mmol) in chloroform (12 mL) under nitrogen. The solvent is removed in vacuo, and the residue is treated as in Example 13 to give the crude free ester. This is purified by column chromatography using silica gel and chloroform/ethyl acetate (9:1) as eluent. The free ester is converted to the salt by treatment with HCl in ether. The resulting solid is washed with ether and recrystallised from hot ethyl acetate/methanol to yield the title compound.

Example 16

(±)-trans-[2-(4-morpholinyl)cyclohexyl]benzo[b] thiophene-4-acetate monohydrochloride (Compound #16)

4-Thianaphtheneacetyl chloride is prepared according to the method described in Example 8 using 4-thianaphtheneacetic acid (2.44 g, 12.8 mmol) to give a red-brown oil which is dissolved in chloroform (15 mL). This solution is refluxed for 27 hours with a solution of (±)-trans-[2-(4-morpholinyl)]cyclohexanol (2.27 g, 13.5 mmol) in chloroform (10 mL) under nitrogen. The solvent is removed in vacuo, and the residue is treated as in Example 13 to give the crude free ester. This is purified by column chromatography using silica gel and chloroform/ethyl acetate (9:1) as eluent. The free ester is converted to the salt by treatment with HCl in ether. The resulting solid is washed with ether and recrystallised from hot methanol to yield the title compound.

Example 17

(±)-trans-[2-(4-morpholinyl)cyclohexyl](4-bromophenyl)acetate monohydrochloride (Compound #17)

4-Bromophenylacetyl chloride is prepared according to the method described in Example 8 using 4-bromophenylacetic acid (2.75 g, 12.8 mmol) to give an oil which is dissolved in chloroform (10 mL). This solution is refluxed for 19 hours with a solution of (±)-trans-[2-(4-morpholinyl)]cyclohexanol (2.25 g, 12.2 mmol) in chloroform (10 mL) under nitrogen. The solvent is removed in vacuo, and the residue is treated as in Example 13 to give the crude free ester, which is then dissolved in 1M hydrochloric acid (70 mL). Sodium chloride (14 g) is added to the solution which is then extracted with chloroform (60 mL then 2×40 mL). The combined extracts are dried over sodium sulfate and the solvent removed in vacuo. The residue is recrystallised from hot ethyl acetate/methanol to give the title compound.

Example 18

(±)-trans-[2-(4-morpholinyl)cyclohexyl]-3,4-dichlorocinnamate monohydrochloride (Compound #18)

3,4-Dichlorocinnamyl chloride is prepared according to the method described in Example 8 using 3,4- dichlorocinnamic acid (2.46 g, 11.4 mmol) to give an oil which is dissolved in chloroform (10 mL). This solution is refluxed for 35 hours with a solution of (±)-trans-[2-(4-morpholinyl)]cyclohexanol (2.0 g, 10.8 mmol) in chloroform (10 mL) under nitrogen. The solvent is removed in vacuo and the residue partitioned between 10% aqueous sodium hydroxide (50 mL) and dichloromethane (50 mL). The aqueous layer is extracted with more dichloromethane (2×50 mL) and the combined extracts are dried over sodium sulfate. The solvent is removed and the crude ester is purified by column chromatography using silica gel and chloroform/ethyl acetate (1:1) as eluent. The free ester is converted to the salt by treatment with HCl in dichloromethane/ether (1:4). The resulting solid is washed with ether and recrystallised from hot methanol to yield the title compound.

Example 19

(±)-trans-[2-(1-piperidinyl)cyclohexyl] thiophenoxyacetate monohydrochloride (Compound #19)

(i) (±)-trans-[2-(1-Piperidinyl)]cyclohexanol is prepared by the method detailed in Example 1(i), refluxing piperidine (14.8 mL, 0.15 mol), cyclohexene oxide (15.5 mL, 0.15 mol) and water (5 mL). The product is purified by full vacuum distillation to give a colorless liquid.

(ii) A chloroform (10 mL) solution of thiophenoxyacetyl chloride, prepared from thiophenoxyacetic acid (1.85 g, 11 mmol) as in Example 8, is refluxed for 12 hours with a solution of (±)-trans-[2-(1-piperidinyl)]cyclohexanol (1.85 g, 10 mmol) in chloroform (15 mL) under nitrogen. The crude product, which precipitates on cooling the mixture, is filtered off and washed with ether. It is recrystallised from hot methanol (4 mL), and washed with ether, to give the title compound.

Example 20

(±)-trans-[2-(4-morpholinyl)cyclohexyl]-2-(1-naphthyl)propionate monohydrochloride (Compound #20)

(i) 1-Naphthylacetic acid (10 g, 53.7 mmol) is dissolved in dry THF (150 mL) under nitrogen. The solution is cooled to −10° C., treated with 1.6M butyl lithium in hexanes (72 mL, 115 mmol), and stirred for 15 minutes. A solution of iodomethane (3.7 mL, 59.4 mmol) in dry THF (50 mL) is added, and the mixture is allowed to warm to room temperature and stir for several hours. The solvent is removed in vacuo, and the residue dissolved in 5% sodium hydroxide solution (500 mL), washed with ether (3×200 mL), and then acidified by the addition of 6N hydrochloric acid. The aqueous is then extracted with dichloromethane (3×200 mL), the organic extracts are dried over sodium sulfate, and the solvent removed to leave 2-(1-naphthyl)propionic acid as a white solid.

(ii) 2-(1-Naphthyl)propionyl chloride, prepared according to the method described in Example 8 using 2-(1-napthyl) propionic acid (2.55 g, 12.8 mmol), is dissolved in chloroform (10 mL). The acid chloride solution is added to a solution of (±)-trans-[2-(4-morpholinyl)]cyclohexanol prepared as in Example 4(i) (2.25 g, 12.2 mmol) in chloroform (10 mL) under nitrogen. The mixture is refluxed for 14 hours. The solvent is removed in vacuo, and the residue is partitioned between 1M hydrochloric acid (150 mL) and ether (100 mL). The ether layer is separated and the aqueous is washed with more ether (2×50 mL), and then basified by the addition of 50% sodium hydroxide solution. This is then extracted with ether (3×50 mL), and the combined ether extracts are washed with water until GC shows no unreacted aminoalcohol in the ether. The ether containing the product is then dried over sodium sulfate, and the solvent is removed to leave the crude free ester. The residue is dissolved in ether (40 mL) and dichloromethane (5 mL) and treated with HCl in ether to precipitate the salt. It is washed with ether and recrystallised from ethyl acetate/methanol to yield the title compound.

Example 21

(±)-(1α,2β,4β,5β)-[4,5-dimethoxy-2-(1-pyrrolidinyl) cyclohexyl]benzofuran-2-acetate monohydrochloride (Compound #21)

(i) Iodine (122 g, 480 mmol) is added gradually over 5 hours to a mixture of 1,4-cyclohexadiene (77 g, 963 mmol) and sodium iodate (51.5 g, 240 mmol) in glacial acetic acid (50 mL). This mixture is stirred for a further 1 hour and then water (17.3 g, 963 mmol) and potassium acetate (94.3 g, 963 mmol) are added and the mixture is refluxed for 3 hours. The acetic acid is removed by vacuum distillation, and the residue is dissolved in ether (400 mL) and washed with saturated sodium metabisulfite solution (400 mL). The aqueous layer is extracted with ethyl acetate (3×80 mL), and the combined organic extracts are dried over sodium sulfate and the solvent removed. The resulting oil is dissolved in ether (200 mL) and treated with 10% potassium hydroxide in methanol until chromatography shows the conversion to cis-4,5-cyclohexenediol to be complete. The mixture is neutralized by the addition of solid carbon dioxide. The solvent is removed and the product is partitioned between saturated sodium chloride solution and ethyl acetate. The ethyl acetate extracts are dried over sodium sulfate, the solvent is removed and the product, cis-4,5-cyclohexenediol, is purified by vacuum distillation (bp 90–100° C. at full vacuum) to give a white solid.

(ii) A solution of the diol (37.1 g, 325 mmol) in dry THF (600 mL) is added over 1 hour to a cooled, stirred suspension of sodium hydride (32 g of a 60% dispersion in mineral oil, 800 mmol) in dry THF (800 mL) under nitrogen. A solution of methyl iodide (60 mL, 964 mmol) in THF (60 mL) is added and the mixture stirred for 12 hours. The reaction is quenched by the addition of moist ether followed by water. The solvent is removed and the residue partitioned between water (200 mL) and ether (300 mL). The aqueous layer is extracted with additional ether (2×75 mL) and the combined organic extracts are dried over sodium sulfate and the solvent removed. The product, 4,5-dimethoxycyclohexene, is purified by vacuum distillation (bp 90° C. at 20 mmHg) to give a colorless oil.

(iii) m-Chloroperbenzoic acid (43 g, 250 mmol) is dissolved in ether (400 mL), any aqueous layer is separated, and the ether solution is dried over sodium sulfate and added quickly dropwise to a solution of 4,5-dimethoxycyclohexene (17.7 g, 125 mmol) in ether (250 mL). The mixture is stirred for 12 hours, most of the ether is removed (450 mL) in vacuo, and dichloromethane is added (400 mL). The solution is washed with 20% sodium metabisulfite solution (3×200 mL), saturated sodium bicarbonate solution (3×200 mL) and brine (3×200 mL). The solvent is removed and the epoxide is refluxed with pyrrolidine (40 mL, 480 mmol) and water (10 mL) for 2 hours. After cooling, 25% sodium hydroxide solution (30 mL) is added and the excess pyrrolidine removed by distillation. The product, 4,5-dimethoxy- 2-(1-pyrrolidinyl)cyclohexanol, is extracted into dichloromethane (3×100 mL) and purified by distillation (bp 90–100° C. at full vacuum).

(iv) Benzofuran-2-acetyl chloride, prepared according to the method described in Example 8 using benzofuran-2-acetic acid (2.1 g, 12 mmol), is dissolved in chloroform (15 mL). This solution is added to a solution of 4,5-dimethoxy-2-(1-pyrrolidinyl)cyclohexanol (2.5 g, 11 mmol) in chloroform (10 mL), and the mixture is refluxed for 11 hours under nitrogen. The solvent is removed in vacuo, and the residue is partitioned between 1M hydrochloric acid (100 mL) and ether (60 mL). The ether layer is separated and the aqueous is washed with more ether (2×30 mL), and then basified by the addition of 50% sodium hydroxide solution. This is then extracted with ether (4×30 mL), and the combined ether extracts are washed repeatedly with water to remove any unreacted aminoalcohol. The ether containing the product is then dried over sodium sulfate, and the solvent is removed to leave the crude free ester. The free ester is converted to the hydrochloride salt by treatment with HCl in ether. The resulting solid is washed with ether and recrystallised from hot methanol to yield the title compound.

Example 22

(±)-trans-{2-[bis(2-methoxyethyl)amino]cyclohexyl}fluorene-9-carboxylate monohydrochloride (Compound #22)

(i) The intermediate aminoalcohol, (±)-trans-{2-[bis(2-methoxyethyl)amino]}cyclohexanol, is prepared by the method detailed in Example 1(i), refluxing bis(2-methoxyethyl)amine (25 mL, 169 mol), cyclohexene oxide (17.2 mL, 170 mmol) and water (8 mL) for 30 hours. The crude product is purified by full vacuum distillation (bp 83–85° C.) to give a clear liquid.

(ii) 9-Fluorenecarboxylic acid (2.43 g, 11.5 mmol) is converted to the corresponding acid chloride according to the method described in Example 8. The resulting white solid is dissolved in chloroform (10 mL) and refluxed under nitrogen with a chloroform solution (10 mL) of (±)-trans-{2-[bis(2-methoxyethyl)amino]}cyclohexanol (2.7 g, 11 mmol) for 20 hours. The solvent is removed in vacuo, and the residue is partitioned between 1M hydrochloric acid (100 mL) and ether (100 mL). The ether layer is separated and the aqueous is washed with more ether (2×50 mL), and then basified by the addition of 50% sodium hydroxide solution. This is then extracted with ether (4×40 mL), and the combined ether extracts are washed repeatedly with water to remove any unreacted aminoalcohol. The ether containing the product is then dried over sodium sulfate, and the solvent is removed to leave the crude free ester. The free ester is converted to the hydrochloride salt by treatment with HCl in ether. The resulting solid is washed with ether and recrystallised from hot methanol to yield the title compound.

Example 23

S-{(±)-trans-[2-(4-morpholinyl)cyclohexyl]}(3,4-dimethoxyphenyl)thioacetate monohydrochloride (Compound #23)

(i) Morpholine (7.6 g, 87 mmol), cyclohexene sulfide (10 g, 88 mmol) and water (5 mL) are refluxed under nitrogen for 5 hours or until GC or tlc analysis show the reaction to be complete. The cooled mixture is partitioned between saturated sodium hydroxide solution (150 mL) and dichloromethane (150 mL). The aqueous layer is washed with dichloromethane (2×50 mL) and the combined organic layers are dried over sodium sulfate. The solvent is removed in vacuo to give (±)-trans-[2-(4-morpholinyl)]cyclohexanethiol which is purified by full vacuum distillation (bp 90–100° C.).

(ii) (3,4-dimethoxyphenyl)acetyl chloride is prepared according to the method described in Example 8 using 3,4-dimethoxyphenylacetic acid (2.85 g, 14.5 mmol) to give a brown oil which is dissolved in chloroform (10 mL). This solution is refluxed for 3 hours with a solution of (±)-trans-[2-(4-morpholinyl)]cyclohexanethiol (2.8 g, 14 mmol) in chloroform (10 mL) under nitrogen. The reaction mixture is partitioned between 1M sodium hydroxide solution (100 mL) and dichloromethane (80 mL). The organic layer is separated and the aqueous is washed with more dichloromethane (2×50 mL). The combined dichloromethane extracts are dried over sodium sulfate, and the solvent is removed to leave the crude free ester. This is purified by column chromatography and converted to the hydrochloride salt by treatment with HCl in ether. The product is recrystallised from hot ethyl acetate/methanol to yield the title compound.

Compounds prepared according to the methods described above were generally characterized by proton and/or carbon-13 NMR and/or infrared spectroscopy. Elemental analysis was obtained for compounds listed in Table 1.

Example 24

S-{(±)-trans-[2-(4-morpholinyl)cyclohexyl]}naphthyl-1-thioacetate monohydrochloride (Compound #24)

1-Naphthylacetyl chloride is prepared according to the method described in Example 8 using 1-naphthylacetic acid (2.0 g, 10.8 mmol) to give a yellow oil which is dissolved in chloroform (10 mL). This solution is added to a solution of (±)-trans-[2-(4-morpholinyl)]cyclohexanethiol (2 g, 10 mmol) in chloroform (10 mL), and the mixture is stirred at room temperature for 8 hours under nitrogen. The solvent is removed and the residue is partitioned between 1M hydrochloric acid (100 mL) and ether (80 mL). The organic layer is separated and the aqueous is washed with more ether (2×60 mL). The aqueous mixture is basified to pH>12 by the addition of 50% sodium hydroxide solution, and extracted with ether (1×80 mL, 2×50 mL). These ether extracts of the basic aqueous solution are washed repeatedly with water to remove any unreacted aminothiol, dried over sodium sulfate, and the solvent is removed to leave the crude free thioester. This is converted to the hydrochloride salt by dissolving it in 1M hydrochloric acid (60 mL), adding sodium chloride (12 g), and extracting with chloroform (3×75 mL). The chloroform is removed in vacuo and the residue is recrystallised from ethyl acetate/methanol to yield the title compound.

Example 25

S-{(±)-trans-{2-[bis(2-methoxyethyl)amino]cyclohexyl}}-4-bromothiobenzoate monohydrochloride (Compound #25)

(i) The intermediate aminothiol, (±)-trans-{2-[bis(2-methoxyethyl)amino]}cyclohexanethiol, is prepared by the method detailed in Example 23(i), refluxing bis(2-methoxyethyl)amine (13 mL, 88 mmol), cyclohexene sulfide (10 g, 88 mmol) and water (8 mL).

(ii) 4-Bromobenzoyl chloride (2.4 g, 11 mmol) in chloroform (10 mL) is added to a solution of (±)-trans-{2-[bis (2-methoxyethyl)amino]}cyclohexanethiol (2 g, 10 mmol) in chloroform (10 mL), and the mixture is stirred at room temperature for 8 hours under nitrogen. The crude free thioester is obtained using the work-up procedure described in Example 24, and is converted to the hydrochloride salt by dissolving it in 1M hydrochloric acid (60 mL), adding sodium chloride (12 g), and extracting with chloroform (3×75 mL). The chloroform is removed in vacuo and the residue is recrystallised from ethyl acetate/methanol to yield the title compound.

Example 26

(±)-trans-[2-(diisopropylamino)cyclohexyl] acenaphthene-1-carboxylate monohydrochloride (Compound #26)

(i) The intermediate aminoalcohol, (±)-trans-(2-diisopropylamino)cyclohexanol, is prepared by the method detailed in Example 1(i), refluxing diisopropylamine (22.3 mL, 170 mmol), cyclohexene oxide (17.2 mL, 170 mmol) and water (8 mL) for 30 hours. The crude product is purified by full vacuum distillation.

(ii) Acenaphthene-1-carboxylic acid (2.28 g, 11.5 mmol) is prepared according to the method described by P. R. Halfpenny et al. in *Synthesis*, 1990, 517–519 or in U.S. Pat. Nos. 4,906,655 and 5,019,588. It is converted to the corresponding acid chloride according to the method described in Example 8, and is dissolved in chloroform (10 mL) and refluxed under nitrogen with a solution of (±)-trans-(2-diisopropylamino)cyclohexanol (2.2 g, 11 mmol) for 20 hours. The solvent is removed in vacuo, and the residue is partitioned between 1M hydrochloric acid (100 mL) and ether (100 mL). The ether layer is separated and the aqueous is washed with more ether (2×50 mL), and then basified by the addition of 50% sodium hydroxide solution. This is then extracted with ether (4×40 mL), and the combined ether extracts are washed repeatedly with water to remove any unreacted aminoalcohol. The ether containing the product is then dried over sodium sulfate, and the solvent is removed to leave the crude free ester. The free ester is converted to the hydrochloride salt by treatment with HCl in ether. The resulting solid is washed with ether and recrystallised from hot acetate/methanol to yield the title compound.

Example 27

(±)-trans-[2-(4-morpholinyl)cyclohexyl] diphenylacetate monohydrochloride (Compound #27)

A solution of diphenylacetylchloride (2.95 g, 128 mmol) in chloroform (10 mL) is slowly added to a solution of (±)-trans-[2-(4-morpholinyl)]cyclohexanol prepared as in Example 4(i) (2.25 g, 12.2 mmol) in chloroform (10 mL) under nitrogen. The mixture is refluxed for 14 hours, and the crude ester is obtained using the work-up procedure described in Example 26. It is dissolved in ether (40 mL) and dichloromethane (5 mL) and treated with HCl in ether to precipitate the salt, which is washed with ether and recrystallised from ethyl acetate/methanol to yield the title compound.

Example 28

(±)-trans-[2-(4-morpholinyl)cyclohexyl]-3-trifluoromethylbenzoate monohydrochloride (Compound #28)

3-(Trifluoromethyl)benzoylchloride (2.96 g, 14.2 mmol), is dissolved in chloroform (15 mL) and is refluxed for 60 hours with a solution of (±)-trans-[2-(4-morpholinyl)] cyclohexanol (2.5 g, 13.5 mmol) in chloroform (12 mL) under nitrogen. The solvent is removed in vacuo, and the residue is treated as in Example 26 to give the crude free ester. This is purified by column chromatography using silica gel and chloroform/ethyl acetate (9:1) as eluent. The free ester is converted to the salt by treatment with HCl in ether. The resulting solid is washed with ether and recrystallised from hot ethyl acetate/methanol to yield the title compound.

Example 29

[7-(1-pyrrolidinyl)-1-oxaspiro[4.5]dec-8-yl] naphthyl-1-acetate monohydrochloride (Compound #29)

(i) 7-(Pyrrolidinyl)-1-oxaspiro[4.5]decan-8-ol is prepared by the method described in Example I(i), refluxing the corresponding epoxide (5 g, 32 mmol, prepared according to the method described in U.S. Pat. No. 4,737,493) with pyrrolidine (2.28 g, 32 mmol) and water (5 mL) under nitrogen until GC or tlc analysis show the reaction to be complete. The produce is purified by fill vacuum distillation.

(ii) The title compound is prepared according to the method described in Example 8 using 1-naphthylacetic acid (2 g, 10.8 mmol) and 7-(pyrrolidinyl)-1-oxaspiro[4.5]decan-8-ol (2.25 g, 10 mmol). The solvent is removed in vacuo, and the residue is treated as in Example 8 to leave the crude free ester. This is dissolved in ether (40 mL) and dichloromethane (5 mL) and treated with HCl in ether to precipitate the salt. It is washed with ether and recrystallised from ethyl acetate/methanol to yield the title compound.

TABLE 1

| Compound | Formula | Calculated | Found |
|---|---|---|---|
| #1 | $C_{18}H_{24}NO_3Cl_3$ | C 52.89, H 5.92, N 3.43% | C 52.59, H 5.78, N 3.37% |
| #3 | $C_{22}H_{30}NO_3Cl_3$ | C 57.09, H 6.53, N 3.03% | C 57.05, H 6.31, N 3.08% |
| #4 | $C_{18}H_{24}NO_4Cl_3$ | C 50.90, H 5.70, N 3.30% | C 50.88, H 5.70, N 3.25% |
| #5 | $C_{20}H_{28}NO_3Cl_3$ | C 54.99, H 6.46, N 3.21% | C 54.31, H 6.49, N 3.26% |
| #6 | $C_{20}H_{26}NO_3ClS$ | C 60.67, H 6.62, N 3.54% | C 60.69, H 6.57, N 3.58% |
| #7 | $C_{18}H_{32}NO_2Cl$ | C 65.53, H 9.78, N 4.25% | C 65.78, N 9.84, N 4.42% |
| #8 | $C_{22}H_{28}NO_3Cl$ | C 67.77, H 7.24, N 3.59% | C 67.47, H 7.21, N 3.57% |
| #9 | $C_{22}H_{28}NO_3Cl$ | C 67.77, H 7.24, N 3.59% | C 67.60, H 7.25, N 3.66% |
| #10 | $C_{18}H_{26}NO_3Cl$ | C 63.61, H 7.71, N 4.12% | C 63.50, H 7.56, N 4.17% |
| #11 | $C_{18}H_{24}NO_3Cl_3$ | C 52.89, H 5.92, N 3.43% | C 52.75, H 5.90, N 3.40% |
| #12 | $C_{18}H_{25}N_2O_5Cl$ | C 56.18, H 6.55, N 7.28% | C 55.85, H 6.48, N 7.20% |

TABLE 1-continued

| Compound | Formula | Calculated | Found |
|---|---|---|---|
| #13 | $C_{23}H_{32}N_2O_2Cl_2$ | C 62.87, H 7.34, N 6.38% | C 62.65, H 7.22, N 6.28% |
| #14 | $C_{23}H_{31}N_2O_2Cl$ | C 68.56, H 7.75, N 6.95% | C 67.63, H 7.52, N 6.91% |
| #15 | $C_{21}H_{26}NO_3Cl$ | C 67.10, H 6.97, N 3.73% | C 67.17, H 6.90, N 3.78% |
| #16 | $C_{20}H_{26}O_3ClS$ | C 60.67, H 6.62, N 3.54% | C 60.40, H 6.53, N 3.51% |
| #17 | $C_{18}H_{25}NO_3ClBr$ | C 51.63, H 6.02, N 3.34% | C 51.56, H 6.01, N 3.34% |
| #18 | $C_{19}H_{26}NO_3Cl_3$ | C 54.24, H 5.75, N 3.33% | C 54.33, H 5.78, N 3.32% |

Example 30
Assessment of Antiarrhythmic Efficacy

Antiarrhythmic efficacy was assessed by investigating the effect of a compound on the incidence of cardiac arrhythmias in conscious rats subject to coronary artery occlusion. Rats weighing 200–300 gms were subjected to preparative surgery and assigned to groups in a random block design. In each case, the animal was anesthetized with halothane during surgical preparation. The left femoral artery was cannulated for measurement of mean arterial blood pressure and withdrawal of blood samples. The left femoral vein was also cannulated for injection of drugs. The thoracic cavity was opened and a polyethylene occluder loosely placed around the left anterior descending coronary artery. The thoracic cavity was then closed. ECG was recorded by insertion of electrodes placed along the anatomical axis of the heart. All cannulae and electrode leads were exteriorized in the mid scapular region. In random and double-blind manner, about 0.5 to 2 hours post-surgery, an infusion of vehicle, or the compound to be tested was given. After 15 minutes infusion, the occluder was pulled so as to produce coronary artery occlusion. ECG, arrhythmias, blood pressure, heart rate and mortality were monitored for 30 minutes after occlusion. Arrhythmias were recorded as ventricular tachycardia (VT) and ventricular fibrillation (VF) and scored according to Curtis, M. J. and Walker, M. J. A., Cardiovasc. Res. 22:656 (1988) (see Table 2).

TABLE 2

Score Description

| | |
|---|---|
| 0 | 0–49 VPBs |
| 1 | 50–499 VPBs |
| 2 | >499 VPBs and/or 1 episode of spontaneously reverting VT or VF |
| 3 | >1 episode of VT or VF or both (<60s total combined duration) |
| 4 | VT or VF or both (60–119s total combined duration) |
| 5 | VT or VF or both (>119s total combined duration) |
| 6 | fatal VF starting at >15 min after occlusion |
| 7 | fatal VF starting at between 4 min and 14 min 59s after occlusion |
| 8 | fatal VF starting at between 1 min and 3 min 59s after occlusion |
| 9 | fatal VF starting <1 min after occlusion |

Where:
VPB = ventricular premature beats
VT = ventricular tachycardia
VF = ventricular fibrillation Rats were excluded from the study if they did not exhibit pre-occlusion serum potassium concentrations within the range of 2.9–3.9 mM. Occlusion is associated with increases in R-wave height and "S-T" segment elevation; and an occluded zone (measured after death by cardiogreen dye perfusion) in the range of 25%–50% of total left-ventricular weight.

Table 3 describes the result of tests of the compounds described therein as values of arrhythmia score at a given dose in micromoles/kg/min.

TABLE 3

| Compound | Dose | AS |
|---|---|---|
| Vehicle | | 7 |
| #2 | 20 | 4 |
| #4 | 5 | 3.6 |
| #5 | 4 | 3 |
| #6 | 5 | 1.8 |
| #8 | 2 | 3 |
| #9 | 4 | 1.3 |
| #10 | 10 | 2.2 |
| #12 | 8 | 3 |
| #15 | 12 | 2 |
| #16 | 8 | 0.3 |

Example 31
Measurement of ECG Parameters

Rats weighing 200–250 gms were used in this example. Animals were anesthetized with 60 mg/kg pentobarbitone i.p. The carotid artery and jugular vein were cannulated for measurement of blood pressure and drug injection, respectively. ECG was recorded by insertion of electrodes placed along the anatomical axis of the heart. All compounds were given as bolus injections.

Various ECG parameters were measured. The most sensitive of these for measuring sodium channel blockade is RSh (J. Pharmacology Methods 27:51–58 (1992)). Table 4 describes the results of the tests as $ED_{25}$ (micromoles/kg) which are the doses required to produce a 25% increase in the parameter measured (ne =not estimated). The increases in P-R interval, QRS interval and RSh indicate cardiac sodium channel blockade while the increase in Q-T interval indicates ancillary cardiac potassium channel blockade which is the property of a type 1a antiarrhythmic.

TABLE 4

| Compound | RSh | PR | QRS | QT |
|---|---|---|---|---|
| #1 | 10 | 17 | ne | 78 |
| #2 | 11 | 23 | ne | 53 |
| #3 | 140 | 140 | 130 | 160 |
| #4 | 10 | 44 | ne | ne |
| #5 | 36 | 43 | 66 | 45 |
| #6 | 100 | ne | ne | 79 |
| #7 | 6 | 84 | ne | 41 |
| #8 | 11 | 20 | 42 | 57 |
| #9 | 13 | ne | ne | 20 |
| #10 | 16 | ne | ne | 25 |
| #12 | 17 | 64 | 82 | 44 |
| #15 | 80 | 340 | 90 | ne |
| #16 | 23 | 230 | 690 | 33 |

Example 32
Assessment of Sodium Channel Blockade

Rats were prepared according to the preceding procedure. Two silver stimulating electrodes were inserted through the chest wall and implanted in the left ventricle. Square wave stimulation was used to determine threshold current for capture, ventricular fibrillation threshold current, and effective refractory period (Howard, P. G. and Walker, M. J. A., *Proc. West. Pharmacol. Soc.* 33:123–127 (1990)). Table 5 contains $ED_{25}$ values for these indices of cardiac sodium channel blockade, where the $ED_{25}$ is the infusion rate in micromoles/kg/minute of compound required to elicit a 25% increase from control. The increases in refractoriness indicate ancillary blockade of potassium channels. The threshold current for capture is represented by "iT". The fibrillation threshold current is represented by "VFT". The effective refracting period is represented by "ERP".

TABLE 5

| Compound | iT | VFT | ERP |
|---|---|---|---|
| #1 | 6 | 3 | 4 |
| #2 | 5 | 2 | 3 |
| #5 | 5 | 4 | 4 |
| #6 | 12 | 9 | 7 |
| #8 | 5 | 2 | 4 |
| #9 | 34 | 7 | 8 |
| #10 | 15 | 11 | 8 |
| #12 | 4 | 5 | 6 |
| #15 | 33 | 18 | 20 |
| #16 | 15 | 2 | 5 |

Example 33

Voltage Clamp Tests

In order to directly measure cardiac sodium channel blockade, standard whole cell voltage clamp tests were carried out using single isolated adult rat cardiac cells. Results in the form of $EC_{50}$ values, which are micromolar concentrations required to produce a 50% reduction in sodium current, are presented in Table 6.

TABLE 6

| Compound | |
|---|---|
| #1 | 200 |
| #2 | 50 |
| #3 | >150 |
| #4 | >500 |
| #6 | 150 |
| #8 | 80 |
| #9 | >100 |
| #10 | >300 |
| #12 | >300 |
| #15 | ne |
| #16 | 225 |

Example 34

Nerve Conduction Blockade

In order to establish the potency of the compounds to block nerve conduction, two in vitro assays were used. The first was the phrenic nerve diaphragm of the rat. The second was the hypogastric nerve vas deferens. Nerve blockade in these preparations is indicative of local anesthetic activity. Compounds were administered to the bath solution in increasing concentrations while the preparations were being stimulated with regular electrical impulses. Table 7 shows the micromolar concentrations at which the twitch response from electrical stimulation is reduced to 50% of control value.

TABLE 7

| | Compound | | | | |
|---|---|---|---|---|---|
| | #1 | #2 | #3 | #5 | #6 |
| Phrenic nerve diaphragm | 90 | 120 | 200 | 180 | 30 |
| Hypogastric nerve vas deferens | 40 | 25 | 300 | 100 | 100 |

Example 35

Opioid-like Effects

During in vivo tests of compound #6, it was observed that this compound induced opioid-like effects on the central nervous system of the rat. These effects were completely blocked by naloxone, an inhibitor of mu, delta and kappa opioid agonists. This provides evidence that some of the compounds may have analgesic activity through activation of opioid receptors. Examination of members of this series of compounds by analgesic assays and binding studies show the presence of opioid binding and activity.

From the foregoing, it will be evident that, although specific embodiments of the invention have been described herein for purposes of illustration, various modifications may be made without deviating from the spirit and scope of the invention.

What is claimed is:

1. An enantiomer or geometric isomer of a compound of formula I, or a solvate or pharmaceutically acceptable salt thereof, said compound of the formula:

(I)

wherein X is a direct bond;
or —$(CH_2)_n$—Y—, where n=1, 2, or 3, and Y is a direct bond, O or S;
or —$CH(R_{12})$—Y—, where $R_{12}$ is alkyl of from one to six carbon atoms, a saturated carbocyclic ring of from three to six carbon atoms, phenyl or benzyl, and Y is a direct bond, O or S;
or —$C(R_{13})$=CH—, where $R_{13}$ is hydrogen, alkyl of from one to six carbon atoms, or phenyl;
$R_1$ and $R_2$, taken together with the nitrogen atom to which they are attached, form a ring denoted by formula II:

(II)

—N⟨$(CH_2)_m$⟩ where m is an integer from three to eight, and said ring may be substituted at any one carbon atom by hydroxy, oxo, alkyl of one to three carbon atoms or alkoxy of one to three carbon atoms, or may be fused at two adjacent carbon atoms with an aromatic or aliphatic carbocyclic ring of six carbon atoms;

$R_3$ and $R_4$ are independently attached to the cyclohexane ring at the 3-, 4-, 5-, or 6-positions, and are independently hydrogen, hydroxy, alkyl of one to six carbon atoms or alkoxy of one to six carbon atoms, or are points of attachment of a spiro five- or six-membered heterocyclic ring containing one oxygen or sulfur atom; and A is an alkyl group of five to twelve carbon atoms, or is a saturated carbocyclic ring of three to six carbon atoms, or is selected from formulae III, IV, V, VI, VII or VIII:

(III)

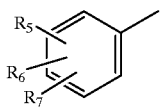

where $R_5$, $R_6$ and $R_7$ are hydrogen, hydroxy, amino, fluorine, chlorine, bromine, nitro, trifluoromethyl, alkyl of one to six carbon atoms, alkoxy of one to six carbon atoms, or aryl, and when X is a direct bond at least one of $R_5$, $R_6$ and $R_7$ is a hydroxy, fluorine, chlorine, bromine, trifluoromethyl, alkyl of from one to six carbon atoms, or aryl substituent, and when X is —CH=CH—, and $R_1$ and $R_2$ when taken together with the nitrogen atom to which they are attached, form a N-phenylpiperazine ring, and $R_3$ and $R_4$ are hydrogen, at least one of $R_5$, $R_6$ and $R_7$ is a substituent other than hydrogen;

(IV)

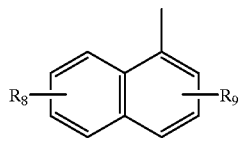

where $R_8$ and $R_9$ are independently hydrogen, hydroxy, fluorine, chlorine, bromine, alkyl of one to six carbon atoms, alkoxy of one to six carbon atoms or aryl;

(V)

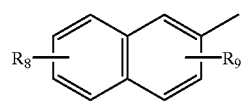

where $R_8$ and $R_9$ are defined as above;

(VI)

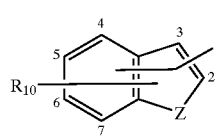

where $R_{10}$ is hydrogen, hydroxy, fluorine, chlorine, bromine, alkyl of from one to six carbon atoms, alkoxy of from one to six carbon atoms, or aryl; Z is $CH_2$, O, S, or N—$R_{11}$ where $R_{11}$ is hydrogen or alkyl of one to six carbon atoms;

(VII)

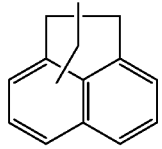

only when X is a direct bond;

(VIII)

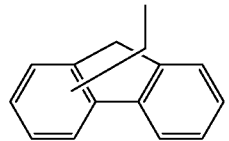

only when X is a direct bond;

with the proviso that, when X is —$(CH_2)_n$—Y—, and n=1, and Y is a direct bond, and $R_1$ and $R_2$, when taken together with the nitrogen atom to which they are attached, form a pyrrolidinyl ring, and $R_3$ and $R_4$ are hydrogen, A may not be 4-thianaphthenyl.

2. An enantiomer or geometric isomer of a compound of formula I, or a solvate or pharmaceutically acceptable salt thereof, said compound of the formula:

(I)

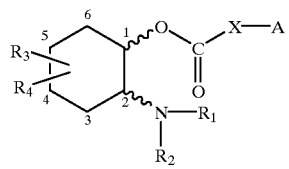

wherein X is a direct bond;

or —$(CH_2)_n$—Y—, where n=1 and Y is a direct bond, O or S;

or —$CH(R_{12})$—, where $R_{12}$ is alkyl of from one to six carbon atoms;

or —$C(R_{13})$=CH—, where $R_{13}$ is hydrogen;

$R_1$ and $R_2$ are defined as in claim 1;

$R_3$ and $R_4$ are defined as in claim 1; and

A is defined as in claim 1;

with the proviso that, when X is —$(CH_2)_n$—Y—, and n=1, and Y is a direct bond, and $R_1$ and $R_2$, when taken together with the nitrogen atom to which they are attached, form a pyrrolidinyl ring, and $R_3$ and $R_4$ are hydrogen, A may not be 4-thianaphthenyl.

3. An enantiomer or geometric isomer of a compound of formula I, or a solvate or pharmaceutically acceptable salt thereof, said compound of the formula:

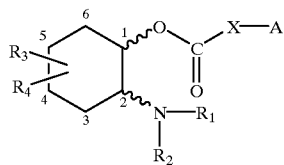

(I)

wherein X is —(CH$_2$)$_n$—Y—, where n=1 and Y is a direct bond or O;
or —CH(R$_{12}$)—, where R$_{12}$ is alkyl of from one to six carbon atoms;
R$_1$ and R$_2$ are defined as in claim 1;
R$_3$ and R$_4$ are independently attached to the cyclohexane ring at the 4- or 5-positions, and are independently hydrogen, alkoxy of one to six carbon atoms, or are points of attachment of a spiro five- or six-membered heterocyclic ring containing one oxygen atom; and
A is an alkyl group of five to twelve carbon atoms, or is a saturated carbocyclic ring of three to six carbon atoms, or is selected from:
formula III where R$_5$, R$_6$ and R$_7$ are independently hydrogen, hydroxy, amino, fluorine, chlorine, bromine, nitro, trifluoromethyl, alkyl of one to six carbon atoms, alkoxy of one to six carbon atoms, or aryl;
or formula IV where R$_8$ and R$_9$ are independently hydrogen, hydroxy, fluorine, chlorine, bromine, alkyl of one to six carbon atoms, alkoxy of one to six carbon atoms or aryl;
or formula V where R$_8$ and R$_9$ are defined as above;
or formula VI where R$_{10}$ is hydrogen, hydroxy, fluorine, chlorine, bromine, alkyl of from one to six carbon atoms, alkoxy of from one to six carbon atoms, or aryl; Z is CH$_2$, O, S, or N—R$_{11}$ where R$_{11}$ is hydrogen or alkyl of one to six carbon atoms;
with the proviso that, when X is —(CH$_2$)$_n$—Y—, and n=1, and Y is a direct bond, and R$_1$ and R$_2$, when taken together with the nitrogen atom to which they are attached, form a pyrrolidinyl ring, and R$_3$ and R$_4$ are hydrogen, A may not be 4-thianaphthenyl.

4. An enantiomer or geometric isomer of a compound of formula X, or a solvate or pharmaceutically acceptable salt thereof, said compound of the formula:

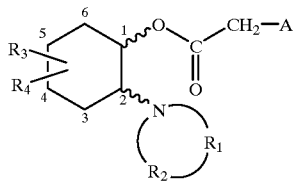

(X)

wherein R$_1$ and R$_2$ are defined as in claim 1;
R$_3$ and R$_4$ are independently attached to the cyclohexane ring at the 4- or 5-positions, and are independently hydrogen, methoxy, or are points of attachment of a five-membered oxaspiran ring; and
A is a saturated carbocyclic ring of from three to six carbon atoms, or is selected from:

formula III where R$_5$ is hydrogen, and R$_6$ and R$_7$ are independently hydrogen, hydroxy, amino, fluorine, chlorine, bromine, nitro, trifluoromethyl, methyl, ethyl, methoxy, or ethoxy, and at least one of R$_6$ and R$_7$ is a substituent other than hydrogen;
or formula IV where R$_8$ and R$_9$ are hydrogen;
or formula V where R$_8$ and R$_9$ are hydrogen;
or formula VI where R$_{10}$ is hydrogen, and Z is CH$_2$, O, S, or N—R$_{11}$ where R$_{11}$ is hydrogen or methyl;
with the proviso that when R$_1$ and R$_2$, taken together with the nitrogen atom to which they are attached, form a pyrrolidinyl ring, and R$_3$ and R$_4$ are hydrogen, A may not be 4-thianaphthenyl.

5. An enantiomer or geometric isomer of a compound of formula I, or a solvate or pharmaceutically acceptable salt thereof, said compound of the formula:

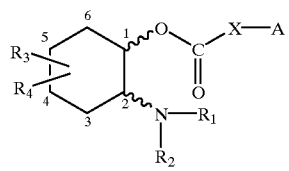

(I)

wherein X is a direct bond or —CH=CH—;
R$_1$ and R$_2$, taken together with the nitrogen atom to which they are attached, form a ring denoted by formula II where m is an integer from three to eight;
R$_3$ and R$_4$ are independently attached to the cyclohexane ring at the 4- or 5-positions, and are independently hydrogen, methoxy, or are points of attachment of a spiro five- or six-membered heterocyclic ring containing one oxygen atom; and
A is a saturated carbocyclic ring of from three to six carbon atoms, or is selected from:
formula III where R$_5$ is hydrogen, and R$_6$ and R$_7$ are independently hydrogen, hydroxy, fluorine, chlorine, bromine, trifluoromethyl, methyl or ethyl, and at least one of R$_6$ and R$_7$ is a substituent other than hydrogen;
or formula IV where R$_8$ and R$_9$ are hydrogen;
or formula V where R$_8$ and R$_9$ are hydrogen;
or formula VI where R$_{10}$ is hydrogen, and Z is O, S, or N—R$_{11}$ where R$_{11}$ is hydrogen or methyl;
or formula VII when X is a direct bond;
or formula VIII when X is a direct bond.

6. An enantiomer or geometric isomer of a compound of formula XII, or a solvate or pharmaceutically acceptable salt thereof, said compound of the formula:

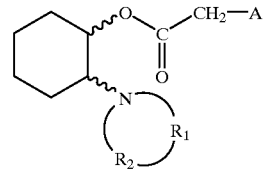

(XII)

wherein R$_1$ and R$_2$, when taken together with the nitrogen atom to which they are attached, form a ring according to formula II where m is an integer from three to eight; and
A is selected from:
formula III where R$_5$ is hydrogen, and R$_6$ and R$_7$ are independently hydrogen, hydroxy, amino, fluorine, chlorine, bromine, nitro, trifluoromethyl, methyl, ethyl, methoxy, or ethoxy, and at least one of R₆ and R₇ is a substituent other than hydrogen;
or formula IV where R₈ and R₉ are hydrogen;
or formula V where R₈ and R₉ are hydrogen;
or formula VI where R₁₀ is hydrogen, and Z is O or S;
with the proviso that, when R₁ and R₂ taken together with the nitrogen atom to which they are attached form a pyrrolidinyl ring, A may not be 4-thianaphthenyl.

7. An enantiomer or geometric isomer of a compound of formula XIII, or a solvate or pharmaceutically acceptable salt thereof, said compound of the formula:

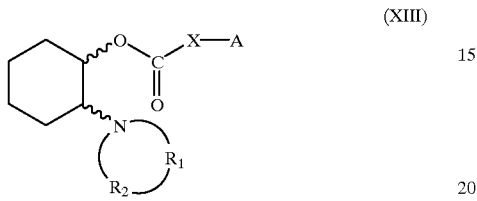

(XIII)

wherein X is a direct bond, trans-CH=CH—, —CH₂— or —CH₂—O—;
R₁ and R₂, when taken together with the nitrogen atom to which they are attached, complete a ring selected from pyrrolidinyl, piperidinyl, hexahydroazepinyl, morpholinyl, or methylpiperazinyl; and
A is selected from cyclohexyl, 3,4-dichlorophenyl, 4-bromophenyl, 1-naphthyl, 2-naphthyl or 3-thianaphthenyl.

8. An enantiomer or geometric isomer of a compound of formula XIV, or a solvate or pharmaceutically acceptable salt thereof, said compound of the formula:

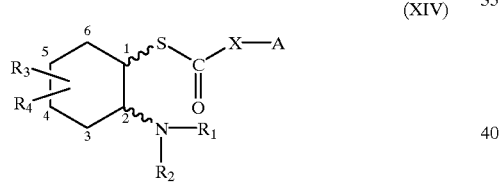

(XIV)

wherein X is a direct bond;
or —(CH₂)ₙ—Y—, where n=1, 2, or 3, and Y is a direct bond, O or S;
or —CH(R₁₂)—Y—, where R₁₂ is alkyl of from one to six carbon atoms, a saturated carbocyclic ring of from three to six carbon atoms, phenyl or benzyl, and Y is a direct bond, O or S;
or —C(R₁₃)=CH—, where R₁₃ is hydrogen, alkyl of from one to six carbon atoms, or phenyl;
R₁ and R₂, taken together with the nitrogen atom to which they are attached, form a ring denoted by formula II:

(II)

where m is an integer from three to eight, and said ring may be substituted at any one carbon atom by hydroxy, oxo, alkyl of one to three carbon atoms or alkoxy of one to three carbon atoms, or may be fused at two adjacent carbon atoms with an aromatic or aliphatic carbocyclic ring of six carbon atoms;

R₃ and R₄ are independently attached to the cyclohexane ring at the 3-, 4-, 5-, or 6-positions, and are independently hydrogen, hydroxy, alkyl of one to six carbon atoms or alkoxy of one to six carbon atoms, or are points of attachment of a spiro five- or six-membered heterocyclic ring containing one oxygen or sulfur atom; and A is an alkyl group of five to twelve carbon atoms, or is a saturated carbocyclic ring of three to six carbon atoms, or is selected from formulae III, IV, V, VI, VII or VIII:

(III)

where R₅, R₆ and R₇ are independently hydrogen, hydroxy, amino, fluorine, chlorine, bromine, nitro, trifluoromethyl, alkyl of one to six carbon atoms, alkoxy of one to six carbon atoms, or aryl, and when X is a direct bond at least one of R₅, R₆ and R₇ is a substituent other than hydrogen;

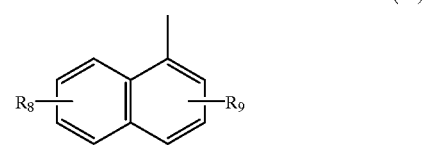

(IV)

where R₈ and R₉ are independently hydrogen, hydroxy, fluorine, chlorine, bromine, alkyl of one to six carbon atoms, alkoxy of one to six carbon atoms or aryl;

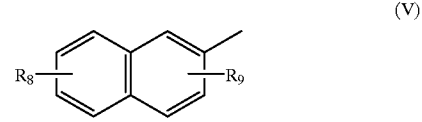

(V)

where R₈ and R₉ are defined as above;

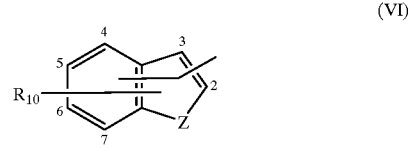

(VI)

where R₁₀ is hydrogen, hydroxy, fluorine, chlorine, bromine, alkyl of from one to six carbon atoms, alkoxy of from one to six carbon atoms, or aryl; Z is CH₂, O, S, or N—R₁₁ where R₁₁ is hydrogen or alkyl of one to six carbon atoms;

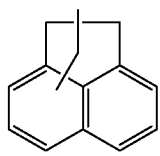

(VII)

only when X is a direct bond;

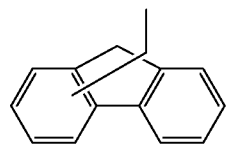

(VIII)

only when X is a direct bond.

9. An enantiomer or geometric isomer of a compound of formula XIV, or a solvate or pharmaceutically acceptable salt thereof, said compound of the formula:

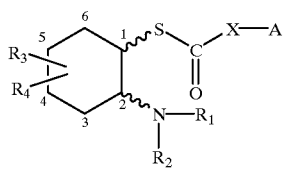

(XIV)

wherein X is a direct bond;
or —(CH$_2$)$_n$—Y—, where n=1, and Y is a direct bond, O or S;
or —CH(R$_{12}$)—, where R$_{12}$ is alkyl of from one to six carbon atoms;
or —C(R$_{13}$)=CH—, where R$_{13}$ is hydrogen;
R$_1$ and R$_2$ are defined as claim 8;
R$_3$ and R$_4$ are independently attached to the cyclohexane ring at the 4- or 5-positions, and are independently hydrogen, alkoxy of one to six carbon atoms, or are points of attachment of a spiro five- or six-membered heterocyclic ring containing one oxygen atom; and
A is defined as in claim 8.

10. A composition comprising a compound according to any one of claims 1—3, 4–5 and 6–9 in combination with a pharmaceutically acceptable carrier or diluent.

11. A method for blocking sodium or potassium ion channels in vitro comprising contacting a preparation containing sodium or potassium ion channels with an effective amount of a compound according to any one of claims 1–3, 4–5 and 6–7.

12. A method for blocking sodium or potassium ion channels in a patient in need thereof comprising administering to said patient an effective amount of a compound according to any one of claims 1–3, 4–5 and 6–7.

13. A method for blocking sodium or potassium ion channels in vitro comprising contacting a preparation containing sodium or potassium ion channels with an effective amount of a compound according to any one of claims 8–9.

14. A method for blocking sodium or potassium ion channels in a patient in need thereof comprising administering to said patient an effective amount of a compound according to any one of claims 8–9.

15. A method for treating arrhythmia comprising administering to a warm-blooded animal an effective amount of an enantiomer or geometric isomer of a compound of formula I, or a solvate or pharmaceutically acceptable salt thereof, said compound of the formula:

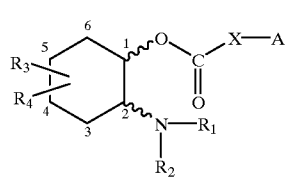

(I)

wherein X is a direct bond;
or —(CH$_2$)$_n$—Y—, where n=1, 2, or 3, and Y is a direct bond, O or S;
or —CH(R$_{12}$)—Y—, where R$_{12}$ is alkyl of from one to six carbon atoms, a saturated carbocyclic ring of from three to six carbon atoms, phenyl or benzyl, and Y is a direct bond, O or S;
or —C(R$_{13}$)=CH—, where R$_{13}$ is hydrogen, alkyl of from one to six carbon atoms, or phenyl;
R$_1$ and R$_2$, taken together with the nitrogen atom to which they are attached, form a ring denoted by formula II:

(II)

where m is an integer from three to eight, and said ring may be substituted at any one carbon atom by hydroxy, oxo, alkyl of one to three carbon atoms or alkoxy of one to three carbon atoms, or may be fused at two adjacent carbon atoms with an aromatic or aliphatic carbocyclic ring of six carbon atoms;

R$_3$ and R$_4$ are independently attached to the cyclohexane ring at the 3-, 4-, 5-, or 6-positions, and are independently hydrogen, hydroxy, alkyl of one to six carbon atoms or alkoxy of one to six carbon atoms, or are points of attachment of a spiro five- or six-membered heterocyclic ring containing one oxygen or sulfur atom; and A is an alkyl group of five to twelve carbon atoms, or is a saturated carbocyclic ring of three to six carbon atoms, or is selected from formulae III, IV, V, VI, VII or VIII:

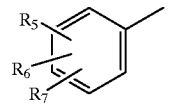

(III)

where R$_5$, R$_6$ and R$_7$ are independently hydrogen, hydroxy, amino, fluorine, chlorine, bromine, nitro, trifluoromethyl, alkyl of one to six carbon atoms, alkoxy of one to six carbon atoms, or aryl;

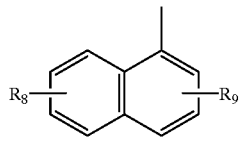
(IV)

where $R_8$ and $R_9$ are independently hydrogen, hydroxy, fluorine, chlorine, bromine, alkyl of one to six carbon atoms, alkoxy of one to six carbon atoms or aryl;

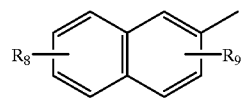
(V)

where $R_8$ and $R_9$ are defined as above;

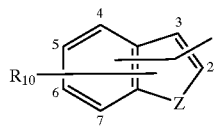
(VI)

where $R_{10}$ is hydrogen, hydroxy, fluorine, chlorine, bromine, alkyl of from one to six carbon atoms, alkoxy of from one to six carbon atoms, or aryl; Z is $CH_2$, O, S, or N—$R_{11}$ where $R_{11}$ is hydrogen or alkyl of one to six carbon atoms;

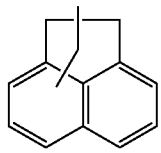
(VII)

only when X is a direct bond;

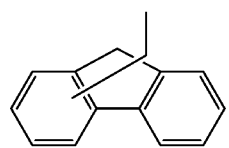
(VIII)

only when X is a direct bond.

16. A method for treating arrhythmia comprising administering to a warm-blooded animal an effective amount of an enantiomer or geometric isomer of a compound of formula XIV, or a solvate or pharmaceutically acceptable salt thereof, said compound of the formula:

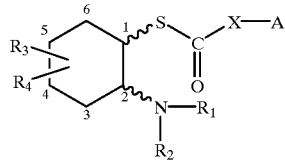
(XIV)

wherein X is a direct bond;

or —$(CH_2)_n$—Y—, where n=1, 2, or 3, and Y is a direct bond, O or S;

or —$CH(R_{12})$—Y—, where $R_{12}$ is alkyl of from one to six carbon atoms, a saturated carbocyclic ring of from three to six carbon atoms, phenyl or benzyl, and Y is a direct bond, O or S;

or —$C(R_{13})$=CH—, where $R_{13}$ is hydrogen, alkyl of from one to six carbon atoms, or phenyl;

$R_1$ and $R_2$, taken together with the nitrogen atom to which they are attached, form a ring denoted by formula II:

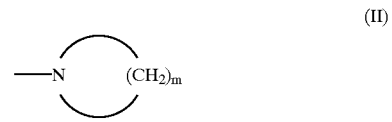
(II)

where m is an integer from three to eight, and said ring may be substituted at any one carbon atom by hydroxy, oxo, alkyl of one to three carbon atoms or alkoxy of one to three carbon atoms, or may be fused at two adjacent carbon atoms with an aromatic or aliphatic carbocyclic ring of six carbon atoms;

$R_3$ and $R_4$ are independently attached to the cyclohexane ring at the 3-, 4-, 5-, or 6-positions, and are independently hydrogen, hydroxy, alkyl of one to six carbon atoms or alkoxy of one to six carbon atoms, or are points of attachment of a spiro five- or six-membered heterocyclic ring containing one oxygen or sulfur atom; and A is an alkyl group of five to twelve carbon atoms, or is a saturated carbocyclic ring of three to six carbon atoms, or is selected from formulae III, IV, V, VI, VII or VIII:

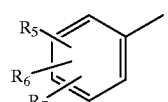
(III)

where $R_5$, $R_6$ and $R_7$ are independently hydrogen, hydroxy, amino, fluorine, chlorine, bromine, nitro, trifluoromethyl, alkyl of one to six carbon atoms, alkoxy of one to six carbon atoms, or aryl;

(IV)

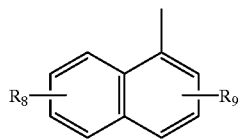

where $R_8$ and $R_9$ are independently hydrogen, hydroxy, fluorine, chlorine, bromine, alkyl of one to six carbon atoms, alkoxy of one to six carbon atoms or aryl;

(V)

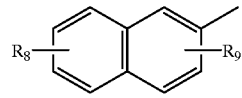

where $R_8$ and $R_9$ are defined as above;

(VI)

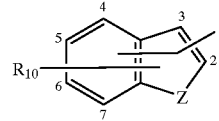

where $R_{10}$ is hydrogen, hydroxy, fluorine, chlorine, bromine, alkyl of from one to six carbon atoms, alkoxy of from one to six carbon atoms, or aryl; Z is $CH_2$, O, S, or $N-R_{11}$ where $R_{11}$ is hydrogen or alkyl of one to six carbon atoms;

(VII)

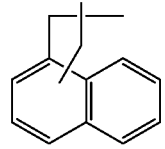

only when X is a direct bond;

(VIII)

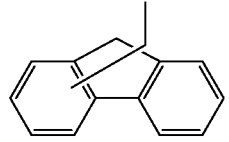

only when X is a direct bond.

* * * * *

UNITED STATES PATENT AND TRADEMARK OFFICE
CERTIFICATE OF CORRECTION

PATENT NO.   : 6,174,879 B1
DATED        : January 16, 2001
INVENTOR(S)  : MacLeod et al.

It is certified that error appears in the above-identified patent and that said Letters Patent is hereby corrected as shown below:

<u>Column 52, claim 16,</u>
Lines 5-15 "

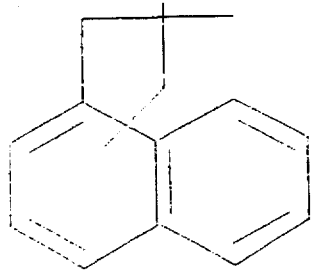

"should read as --

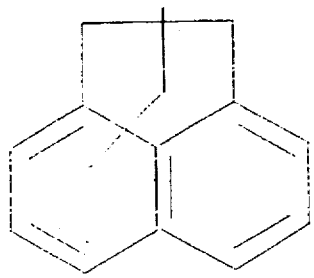

--.

Signed and Sealed this

Twenty-seventh Day of November, 2001

Attest:

*Attesting Officer*

NICHOLAS P. GODICI
*Acting Director of the United States Patent and Trademark Office*